(12) United States Patent
Tada et al.

(10) Patent No.: US 11,383,067 B2
(45) Date of Patent: Jul. 12, 2022

(54) MEDICAL ELONGATED BODY

(71) Applicant: TERUMO KABUSHIKI KAISHA, Tokyo (JP)

(72) Inventors: Yuichi Tada, Tokyo (JP); Takashi Kitaoka, Hadano (JP); Mizuho Hirao, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 163 days.

(21) Appl. No.: 16/276,757

(22) Filed: Feb. 15, 2019

(65) Prior Publication Data

US 2019/0175874 A1    Jun. 13, 2019

Related U.S. Application Data

(63) Continuation of application No. PCT/JP2017/029451, filed on Aug. 16, 2017.

(30) Foreign Application Priority Data

Aug. 16, 2016 (JP) .............................. JP2016-159549

(51) Int. Cl.
  *A61M 25/01* (2006.01)
  *A61M 25/00* (2006.01)
  (Continued)

(52) U.S. Cl.
  CPC ......... *A61M 25/0138* (2013.01); *A61B 1/005* (2013.01); *A61B 1/00078* (2013.01); (Continued)

(58) Field of Classification Search
  CPC . A61B 1/005; A61B 1/00078; A61B 17/3431; A61B 17/1631; (Continued)

(56) References Cited

U.S. PATENT DOCUMENTS 6,053,922 A     4/2000 Edwards et al.
6,656,195 B2 *  12/2003 Peters .............. A61B 17/32002
                                                    606/159
(Continued)

FOREIGN PATENT DOCUMENTS

JP    H11509752 A      8/1999
JP    2009540952 A    11/2009
(Continued)

OTHER PUBLICATIONS www.worktop-express.co.uk/information_guides/choosing-island-worktops-to-create-striking-kitchen-centerpiece/. (Year: 2012).*
(Continued)

*Primary Examiner* — Kathleen S Holwerda
*Assistant Examiner* — Uyen N Vo
(74) *Attorney, Agent, or Firm* — Buchanan Ingersoll & Rooney PC

(57) ABSTRACT

A medical elongated body is disclosed that suppresses elongation in an axial direction while maintaining high flexibility and has high torque transmission capability even in a bent state. The medical elongated body includes a tube shaped body. The tube shaped body has a slit extending in a spiral shape while meandering, the slit is formed from a pair of a first opposing surface and a second opposing surface, the first opposing surface forms a first convex portion, the first convex portion has a first wide portion having a width wider in a circumferential direction Y, the second opposing surface forms a first concave portion which surrounds and accommodates the first wide portion, the first convex portion has a first plane portion and a first side portion connected to both end portions, and in a circumferential developed view, the first side portion and the first plane portion have tangential discontinuity.

16 Claims, 17 Drawing Sheets

(51) Int. Cl.
*A61B 1/00* (2006.01)
*A61B 17/3207* (2006.01)
*A61B 1/005* (2006.01)
*A61B 17/00* (2006.01)
*A61B 1/01* (2006.01)

(52) U.S. Cl.
CPC ..... *A61B 17/320758* (2013.01); *A61M 25/00* (2013.01); *A61M 25/0013* (2013.01); *A61M 25/0051* (2013.01); *A61B 1/01* (2013.01); *A61B 2017/00309* (2013.01); *A61M 2025/0059* (2013.01)

(58) Field of Classification Search
CPC . A61B 2017/00309; A61B 2017/2905; A61M 25/00; A61M 25/0013; A61M 25/0138; A61M 25/0051; A61M 2025/0059
See application file for complete search history.

(56) References Cited

U.S. PATENT DOCUMENTS

| | | | | |
|---|---|---|---|---|
| 2002/0038129 | A1* | 3/2002 | Peters | A61B 17/32002 606/167 |
| 2009/0182416 | A1* | 7/2009 | Forster | A61M 25/0043 623/2.11 |
| 2011/0034764 | A1* | 2/2011 | Verbeek | A61B 1/0055 600/101 |
| 2012/0116247 | A1 | 5/2012 | Wawrzyniak et al. | |
| 2014/0114312 | A1* | 4/2014 | Krause | A61B 17/866 606/62 |
| 2016/0082225 | A1 | 3/2016 | Kobayashi | |

FOREIGN PATENT DOCUMENTS

| | | |
|---|---|---|
| JP | 2014504890 A | 2/2014 |
| WO | 2014174661 A1 | 10/2014 |

OTHER PUBLICATIONS

International Search Report (PCT/ISA/210) dated Oct. 17, 2017, by the Japan Patent Office as the International Searching Authority for International Application No. PCT/JP2017/029451.

Written Opinion (PCT/ISA/237) dated Oct. 17, 2017, by the Japan Patent Office as the International Searching Authority for International Application No. PCT/JP2017/029451.

\* cited by examiner

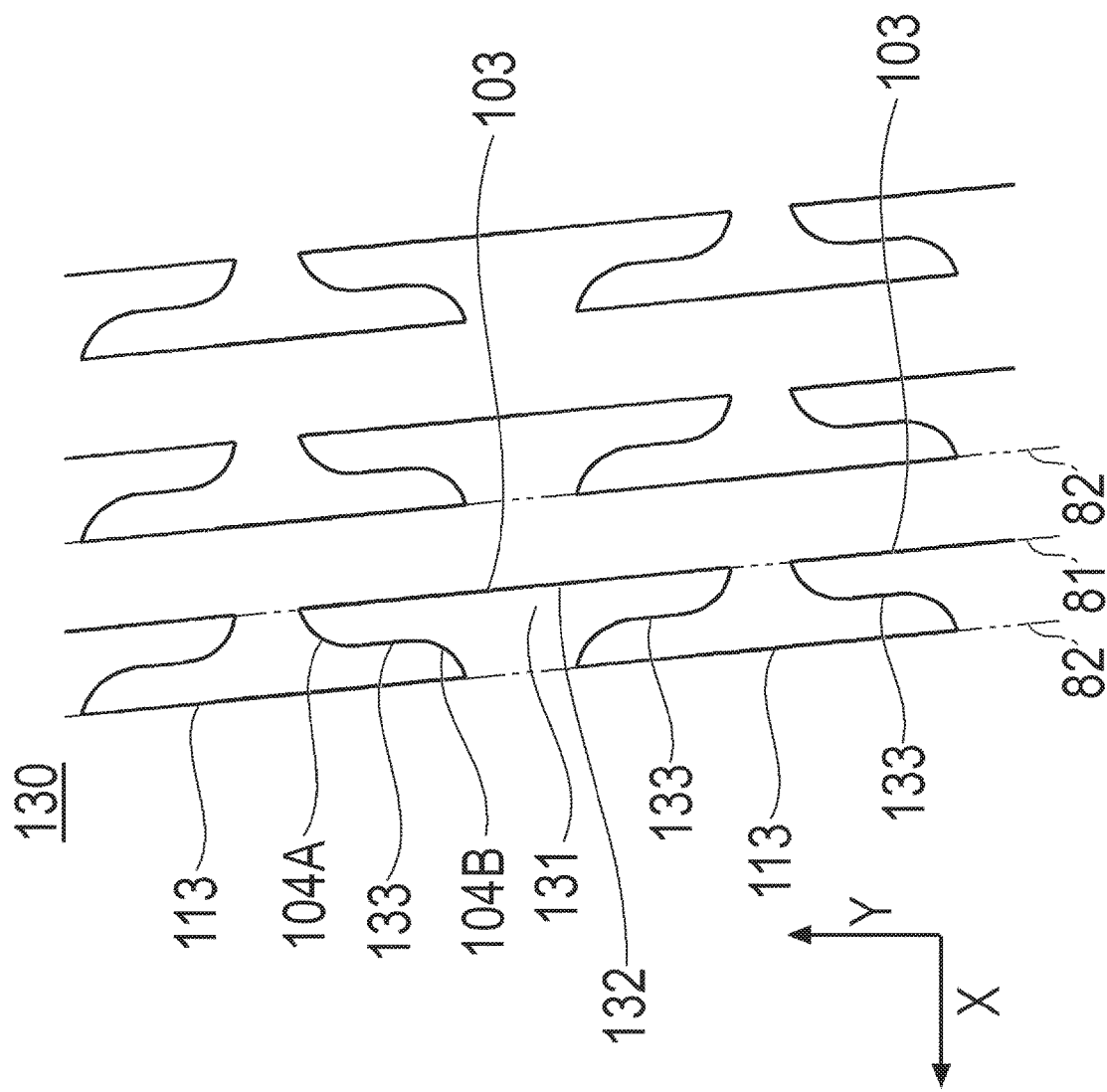

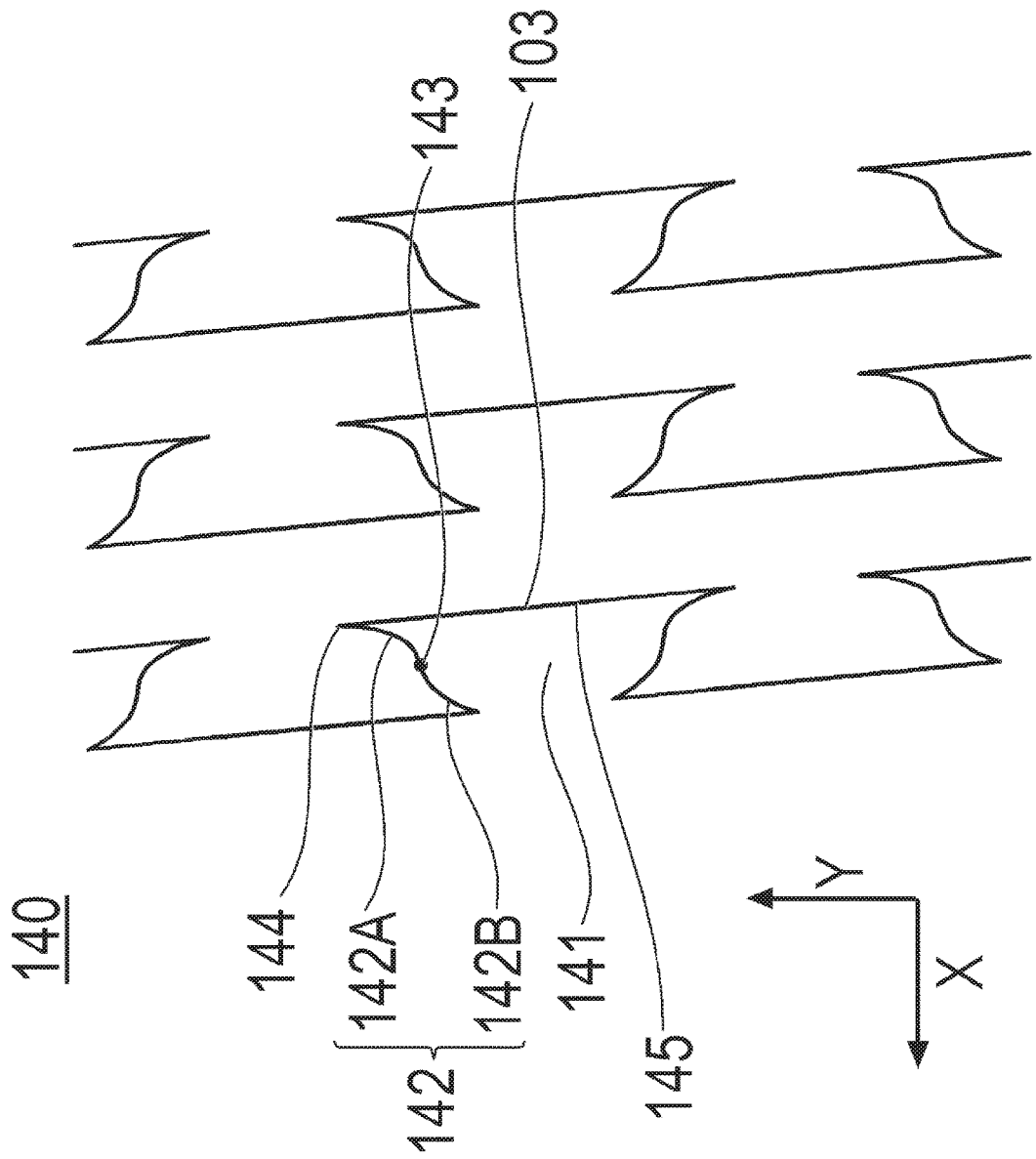

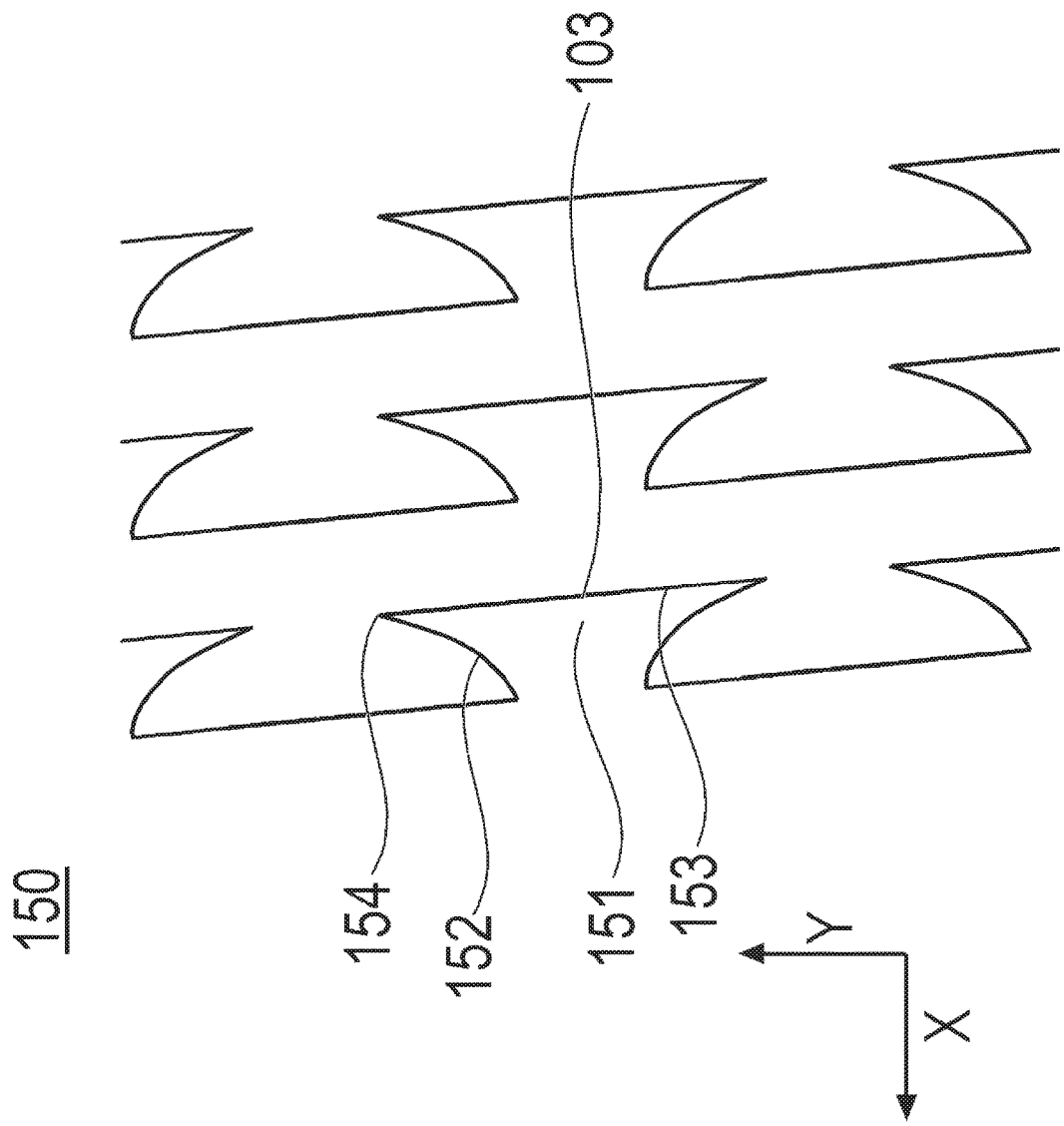

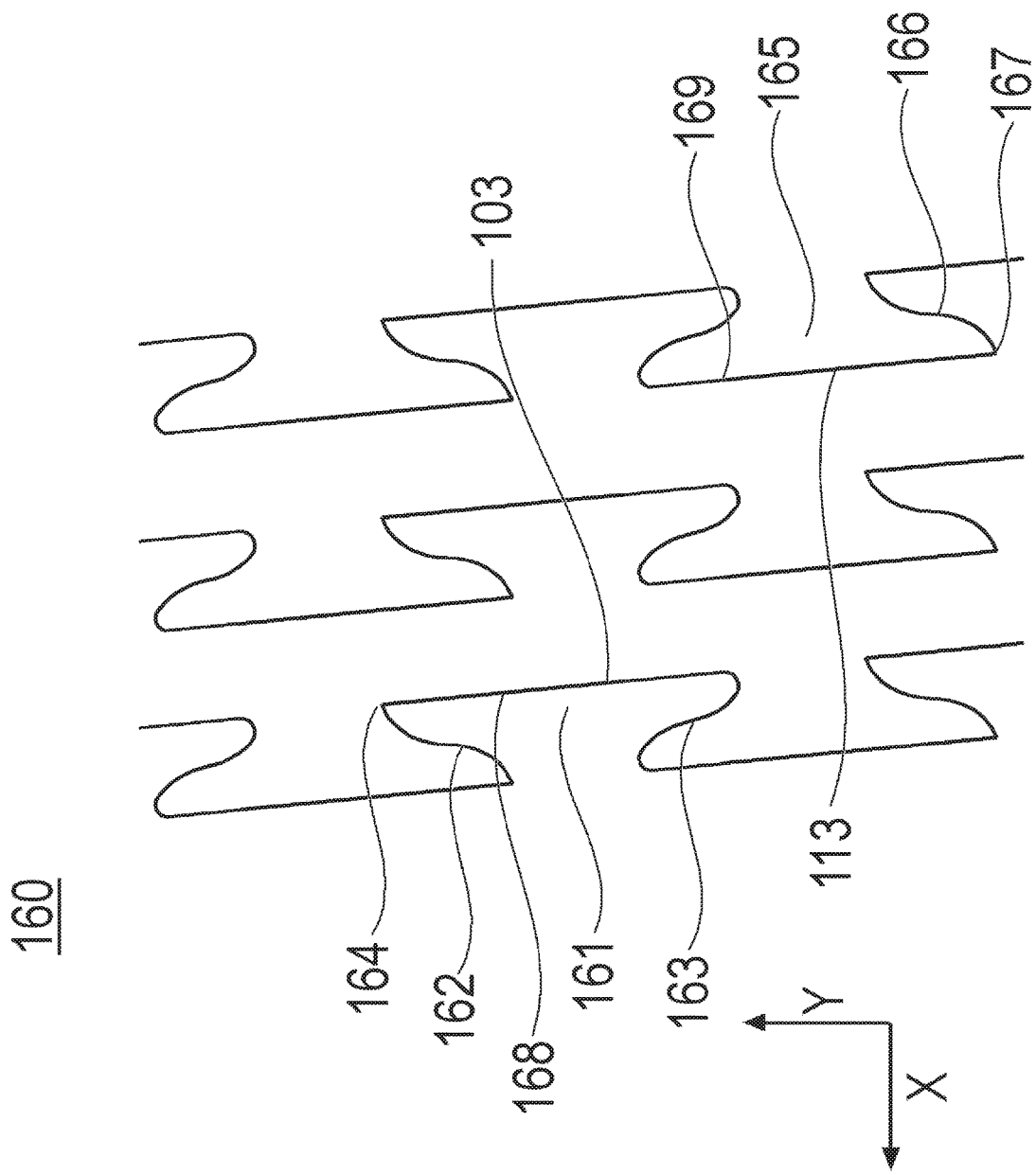

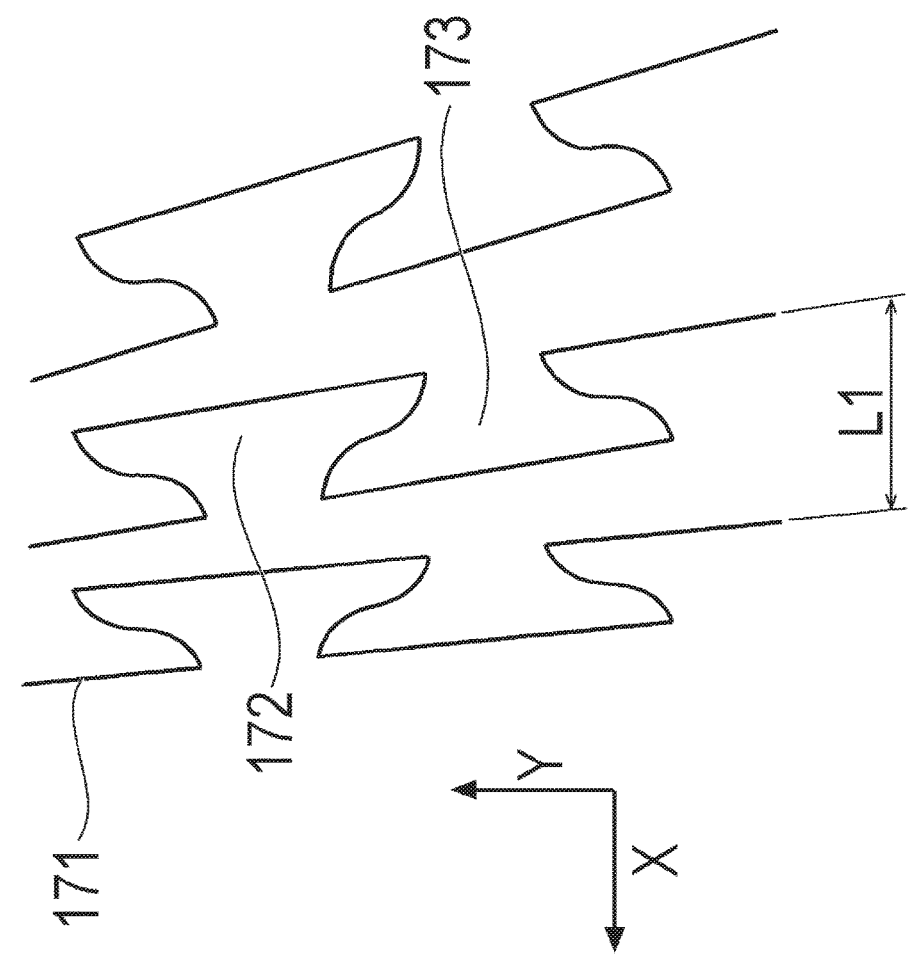

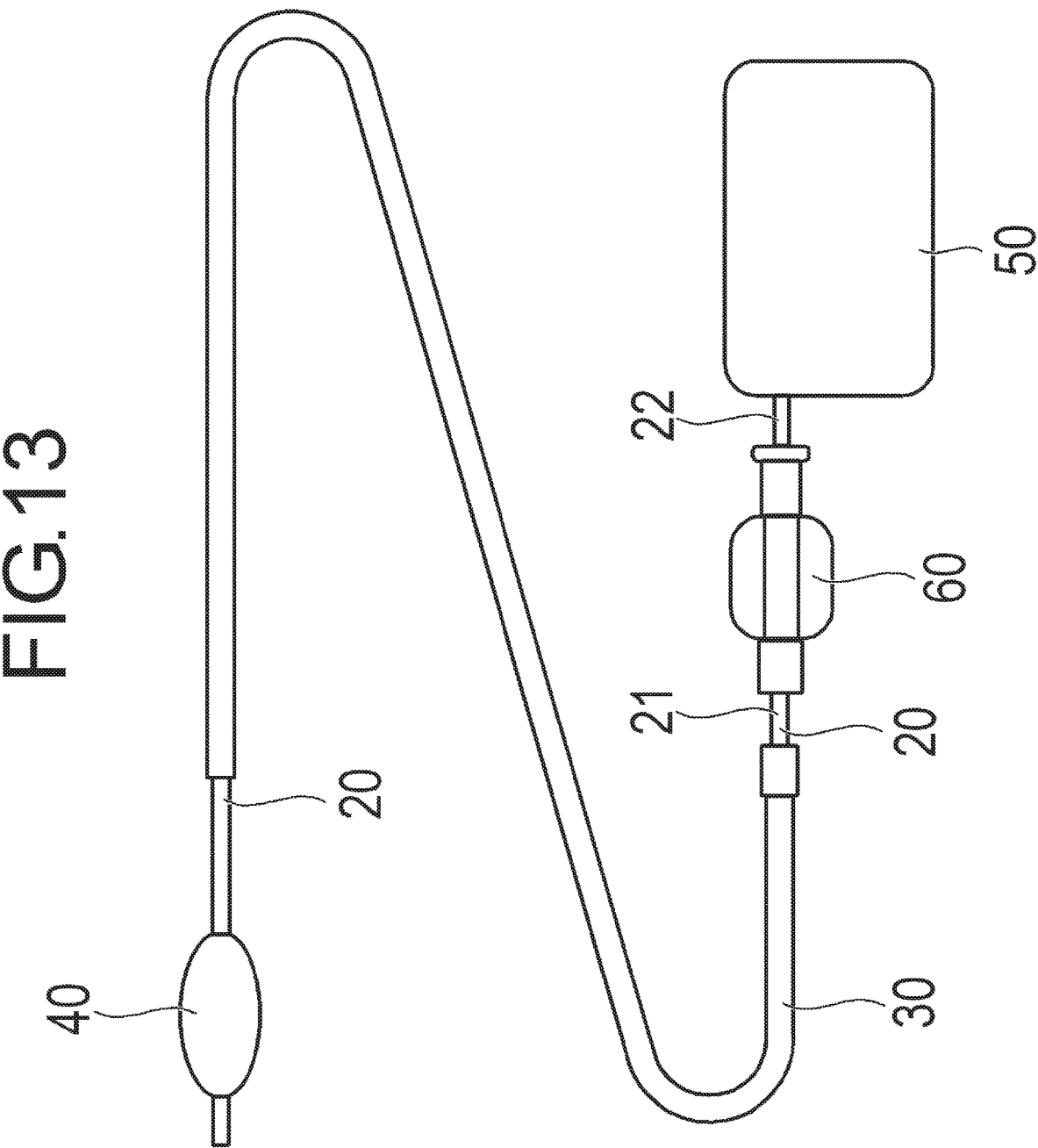

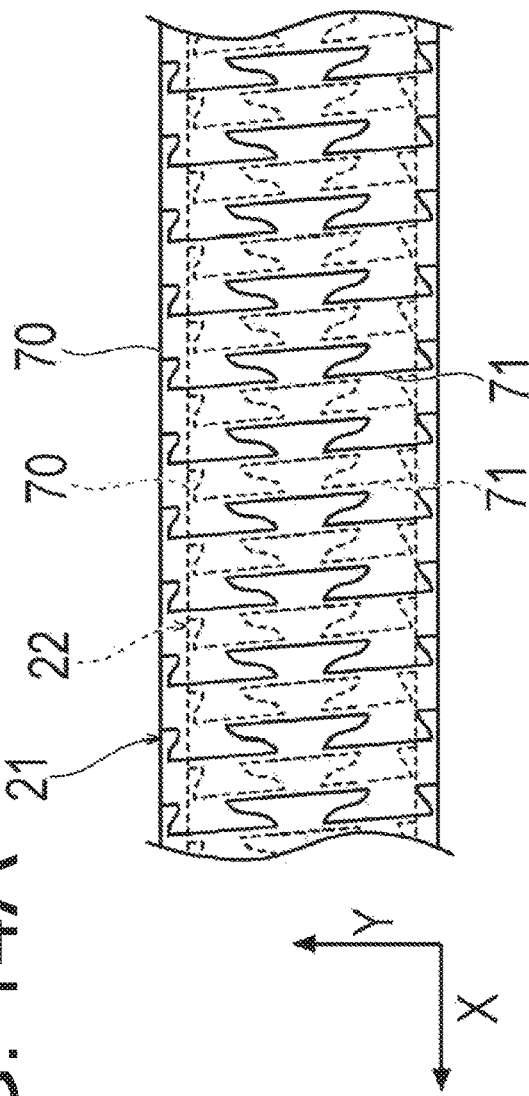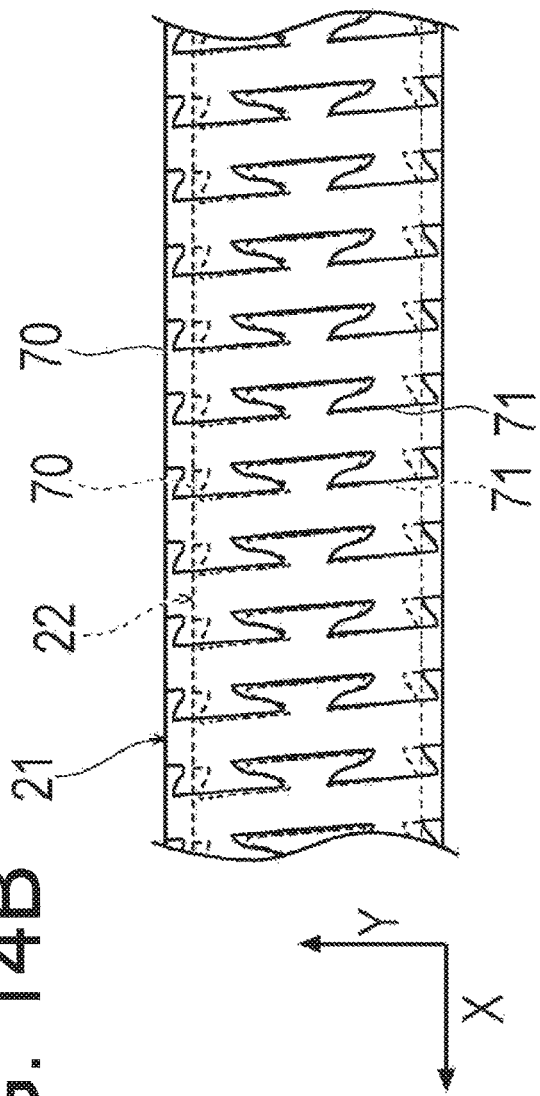

MEDICAL ELONGATED BODY

CROSS-REFERENCES TO RELATED APPLICATIONS

This application is a continuation of International Application No. PCT/JP2017/029451 filed on Aug. 16, 2017, which claims priority to Japanese Patent Application No. 2016-159549 filed on Aug. 16, 2016, the entire content of both of which is incorporated herein by reference.

TECHNICAL FIELD

The present disclosure generally relates to a medical elongated body to be inserted into a biological lumen.

DESCRIPTION

A device having a tube shaped medical elongated body used in a catheter and the like needs to have flexibility and torque transmission performance to a distal end to reach a target site along a shape of a biological lumen in the biological lumen. As a method of making the tube shaped medical elongated body flexible, a method is known of providing a spiral slit in a tube shaped body provided in the medical elongated body. However, the medical elongated body provided with a spiral slit is flexible, while the expansion and contraction in an axial direction is allowed. Furthermore, since the spiral can contract (winding is tight) and expand (winding is loose), twisting occurs in the medical elongated body, and the torque transmission performance to the distal end tends to deteriorate. Accordingly, the medical elongated body capable of reducing the twisting tendency caused by the spiral slit is used. For example, WO 2014/174661 discloses a medical elongated body provided with a convex portion on one side of a pair of opposing surfaces forming a spiral slit and a concave portion in which the convex portion is accommodated on the other side of the opposing surfaces. In such a medical elongated body, since the convex portion is accommodated in the concave portion, the convex portion is caught in the concave portion in a circumferential direction so that the occurrence of twisting can be suppressed.

However, the convex portion of the medical elongated body disclosed in WO 2014/174661 can escape from the concave portion. Accordingly, with the above-described medical elongated body, it is possible to suppress the occurrence of twisting, but it can be difficult to suppress elongation in an axial direction. In addition, when the above-described medical elongated body bends, the convex portion is partially or entirely released from the concave portion, so that it becomes difficult to suppress the twisting, and torque transmission capability deteriorates.

SUMMARY

A medical elongated body is disclosed, which is capable of suppressing elongation in an axial direction while maintaining high flexibility, and having high torque transmission capability even in a bent state.

A medical elongated body is disclosed that includes a tube shaped body, in which the tube shaped body has a slit extending in a spiral shape while meandering, the slit is formed from a pair of a first opposing surface and a second opposing surface, the first opposing surface forms a first convex portion, the first convex portion has a wide portion having a width wider in a circumferential direction of the tube shaped body, the second opposing surface forms a concave portion which surrounds and accommodates the wide portion, the first convex portion has a plane portion and two side portions connected to both end portions of the plane portion in the circumferential direction, and in a circumferential developed view, the side portions and the plane portion have tangential discontinuity.

In the medical elongated body configured as described above, since the first convex portion has a width wider on the protruding side, the first convex portion is caught in the concave portion of the second opposing surface, so that it is possible to suppress the elongation in the axial direction and the occurrence of twisting which causes deterioration in torque transmission capability. Moreover, the side portions and the plane portion intersect in a tangential discontinuity, so that the first opposing surface and the second opposing surface are engaged with each other at a tangentially discontinuous site in a state where the torque is applied in the medical elongated body. Accordingly, the first opposing surface and the second opposing surface are in an interlocked state, and the torque transmission capability of the medical elongated body improves.

In accordance with an aspect, a medical elongated body is disclosed comprising: a tube shaped body, the tube shaped body having a slit extending in a spiral shape while meandering, the slit being formed from a first opposing surface and a second opposing surface; the first opposing surface forming a first convex portion, the first convex portion having a wide portion having a width widening in a circumferential direction of the tube shaped body; the second opposing surface forming a concave portion that surrounds and accommodates the wide portion of the first convex portion, the first convex portion having a plane portion and two side portions, the two side portion being connected to both end portions of the plane portion of the first convex portion in the circumferential direction; and wherein the two side portions and the plane portion have tangential discontinuity.

In accordance with another aspect, a medical elongated body is disclosed comprising: a tube shaped body provided with a belt portion which is a plate member extending in a spiral shape, the belt portion having two side surfaces, each of the two side surfaces having a mountain shape and a valley shape; each of the mountain shape and the valley shape having a width wider in an extending direction of the belt portion at a top surface side of the mountain and at the bottom side of the valley; and a connection surface connecting a top surface of the mountain and a bottom of the valley of the mountain shape and the valley shape having an S shape.

In accordance with an aspect, a method is disclosed of cutting a calcified lesion area in a blood vessel, the method comprising: directing a medical elongated body in the blood vessel to a proximal side of the of the calcified lesion area, the medical elongated body including an elongated shaft portion and a cutting portion, the elongated shaft portion having a tube shaped body having a slit extending in a spiral shape, the slit being formed from a first opposing surface and a second opposing surface, the first opposing surface forming a first convex portion, the first convex portion having a wide portion having a width widening in a circumferential direction of the tube shaped body, the second opposing surface forming a concave portion that surrounds and accommodates the wide portion of the first convex portion, the first convex portion having a plane portion and two side portions, the two side portion being connected to both end portions of the plane portion of the first convex portion in the circumferential direction, and wherein the two side portions and the plane portion have tangential discontinuity; advancing the elongated shaft portion and the cutting portion into the lesion area; rotating the elongated shaft portion and the cutting portion; and causing the cutting portion to come into contact with the lesion area and cutting the lesion area

BRIEF DESCRIPTION OF DRAWINGS

FIG. 8 is a developed view showing a portion of a tube shaped body of a first modification example in the circumferential direction.

FIG. 9 is a developed view showing a portion of a tube shaped body of a second modification example in the circumferential direction.

FIG. 10 is a developed view showing a portion of a tube shaped body of a third modification example in the circumferential direction.

FIG. 11 is a developed view showing a portion of a tube shaped body of a fourth modification example in the circumferential direction.

FIG. 12 is a developed view showing a portion of a tube shaped body of a fifth modification example in the circumferential direction.

FIG. 13 is a plane view showing a sixth modification example.

FIG. 14A is a plane view showing a portion of a shaft portion of a seventh modification example, and 14B is a plane view showing a portion of the shaft portion of an eighth modification example.

DESCRIPTION OF EMBODIMENTS

Figure 1:
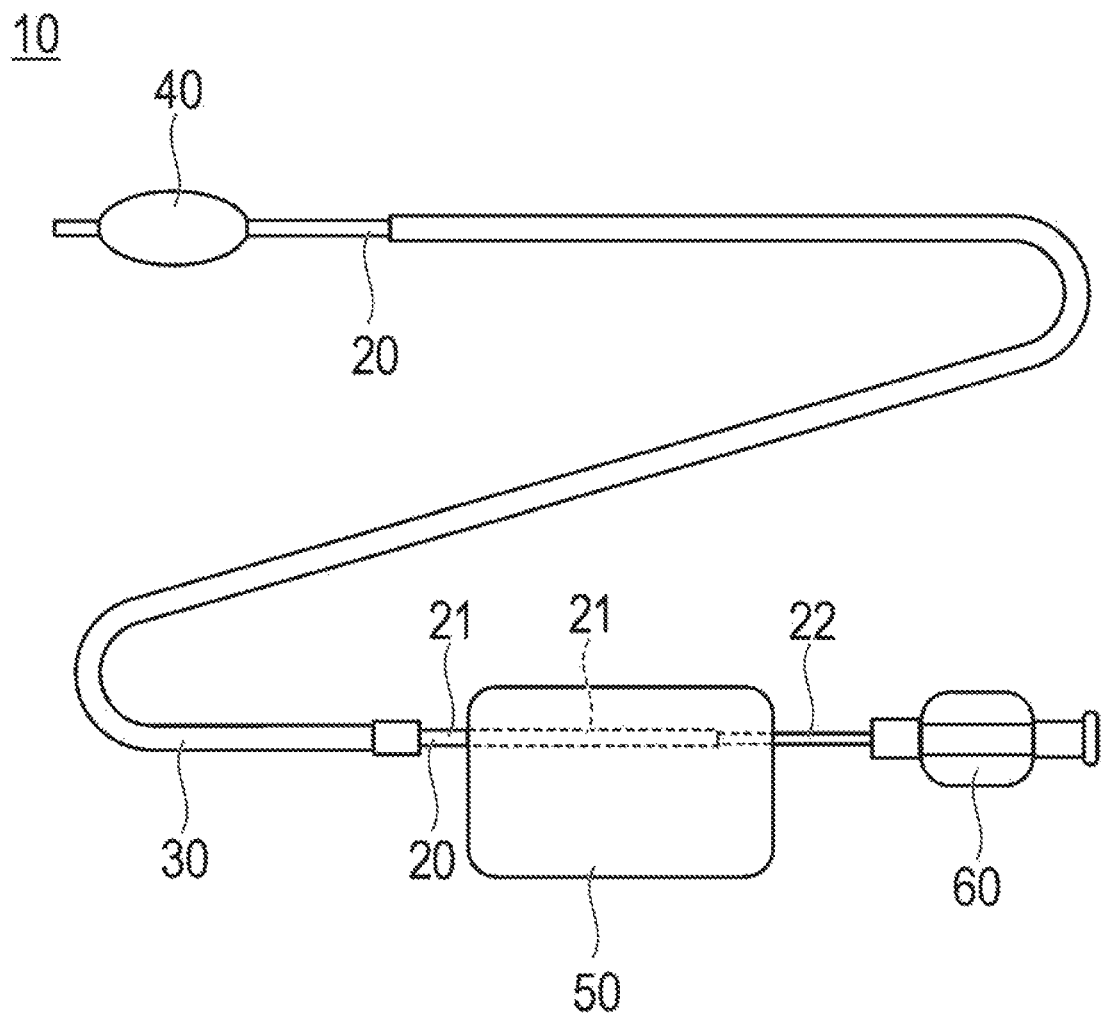
FIG. 1 is a plane view showing a medical elongated body according to an embodiment.
Figure 2:
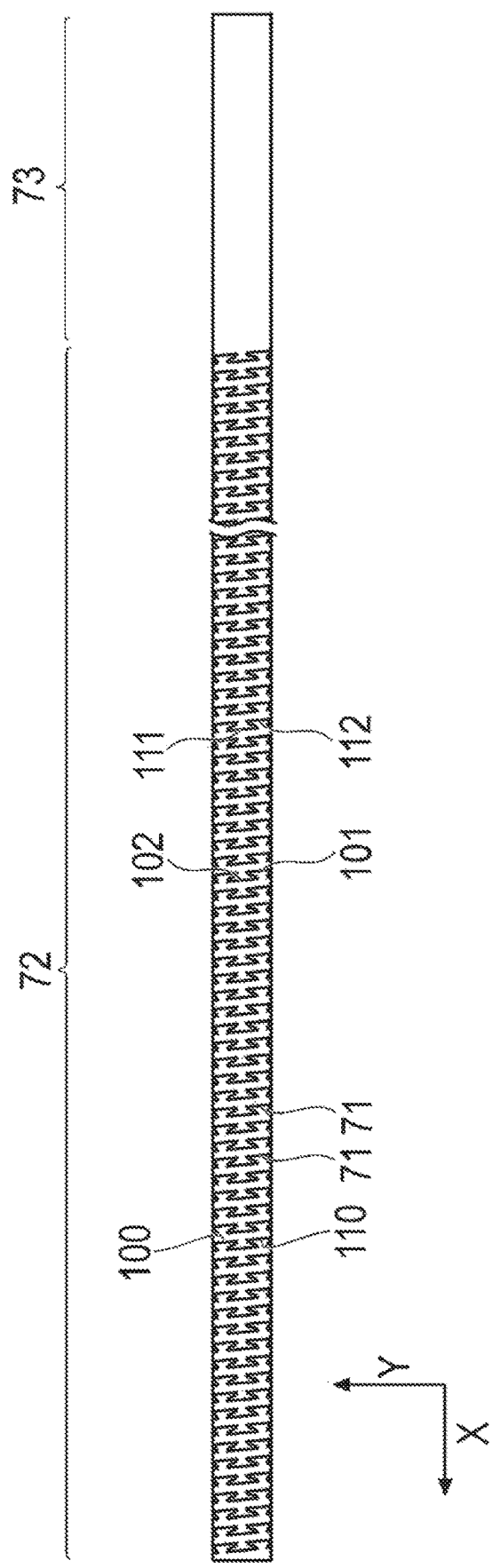
FIG. 2 is a plane view showing a tube shaped body.
Figure 3:
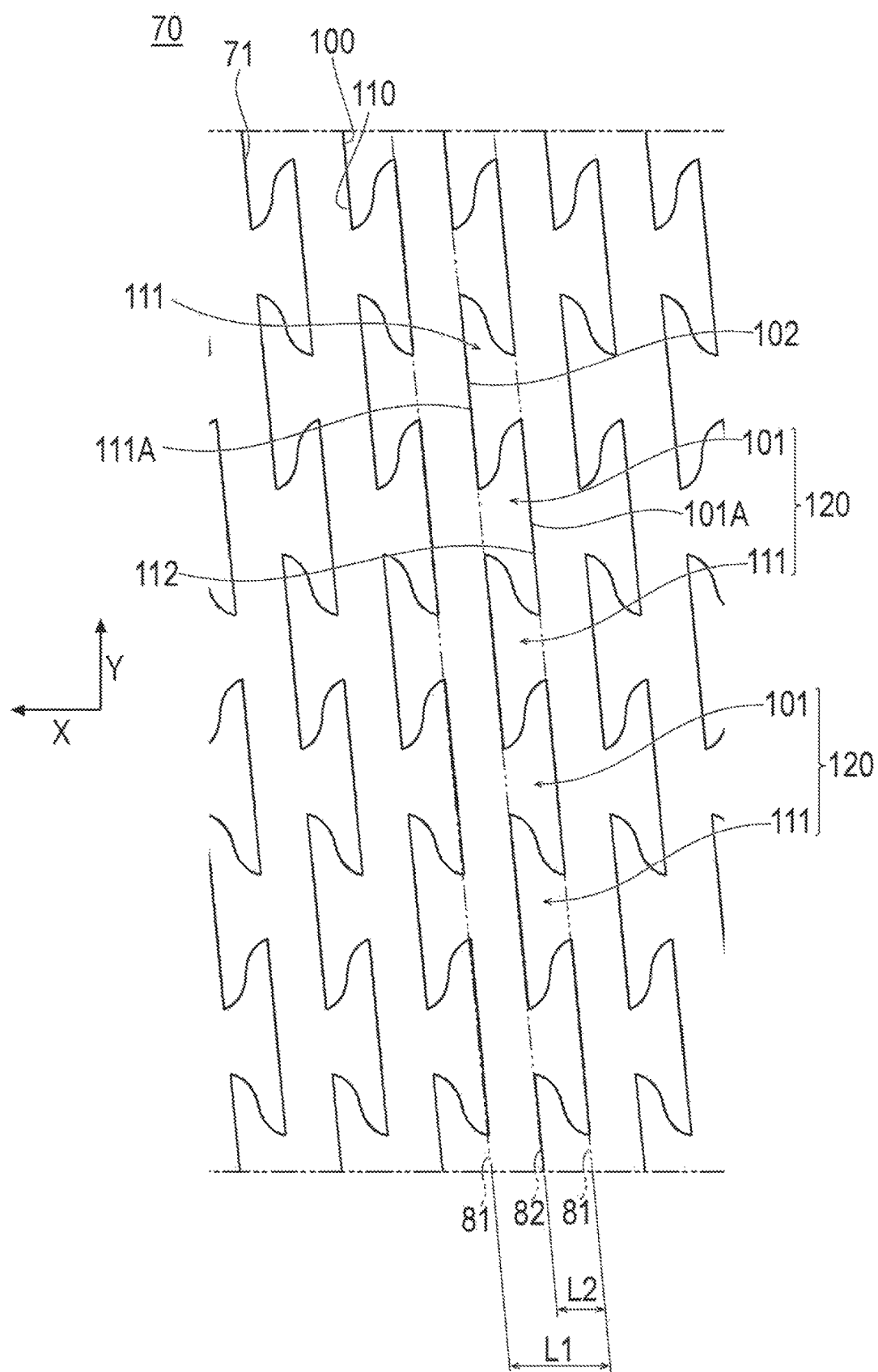
FIG. 3 is a developed view showing a portion of the tube shaped body in a circumferential direction.
Figure 4:
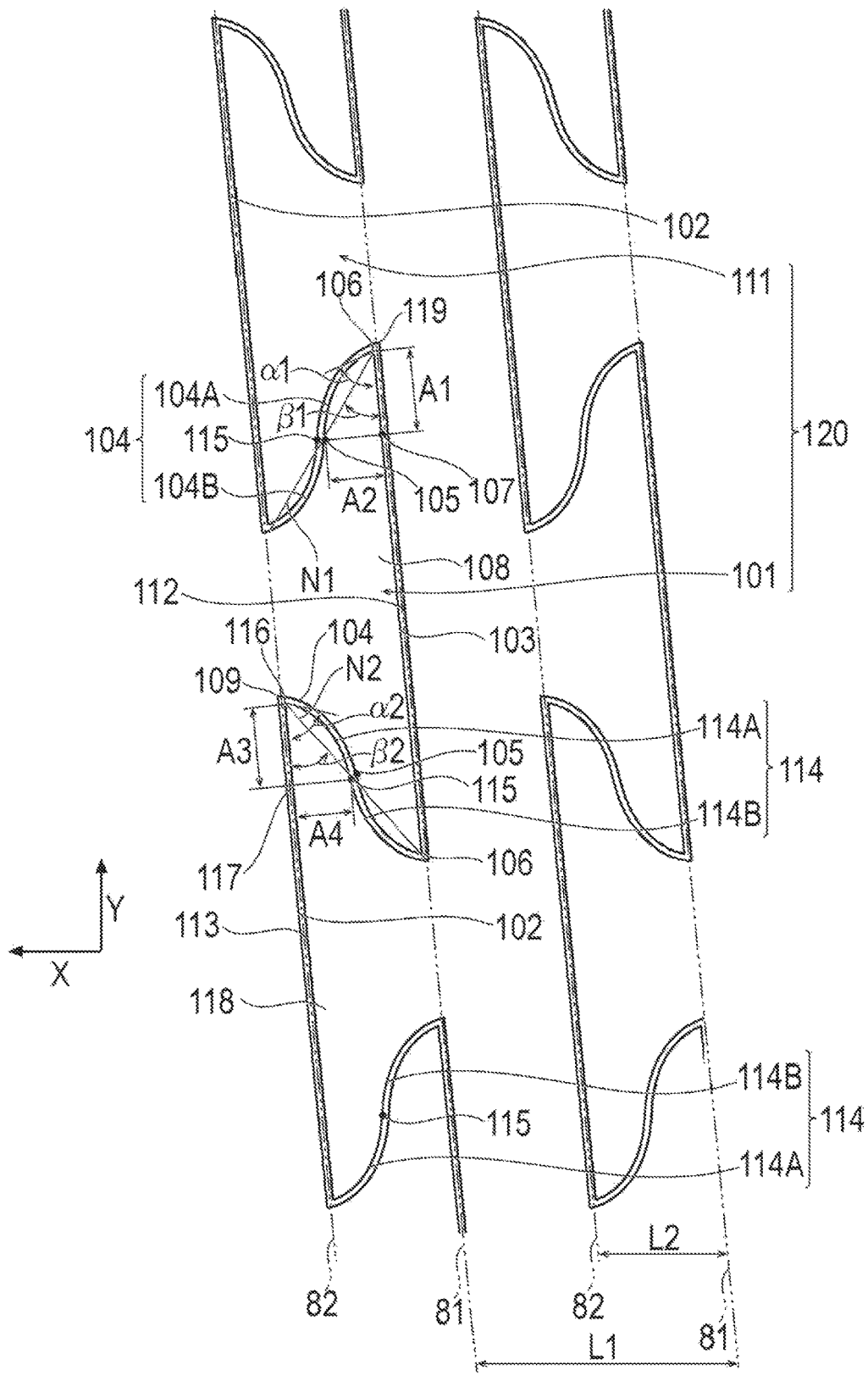
FIG. 4 is a developed view showing a portion of the tube shaped body in the circumferential direction.
Figure 5:
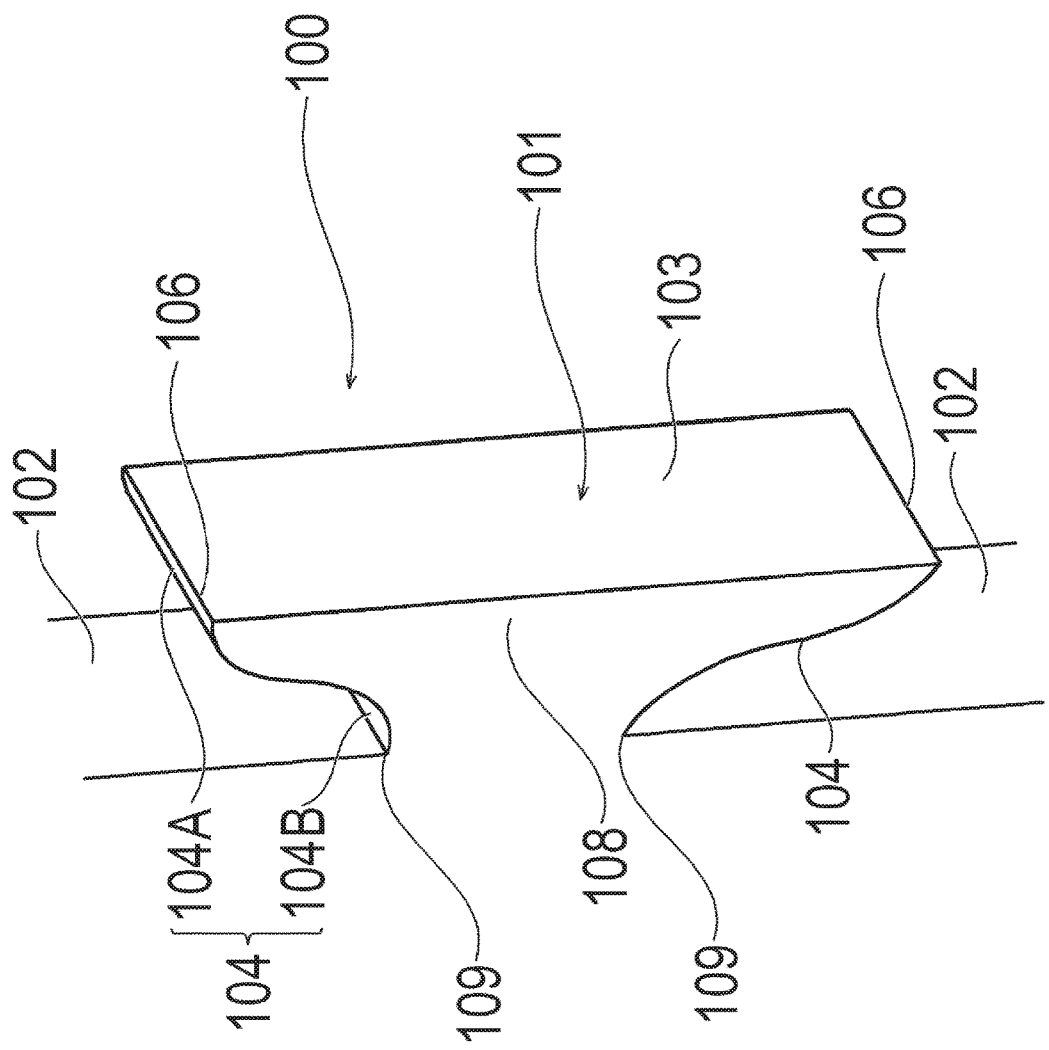
FIG. 5 is a perspective view showing a first opposing surface.
Figure 6:
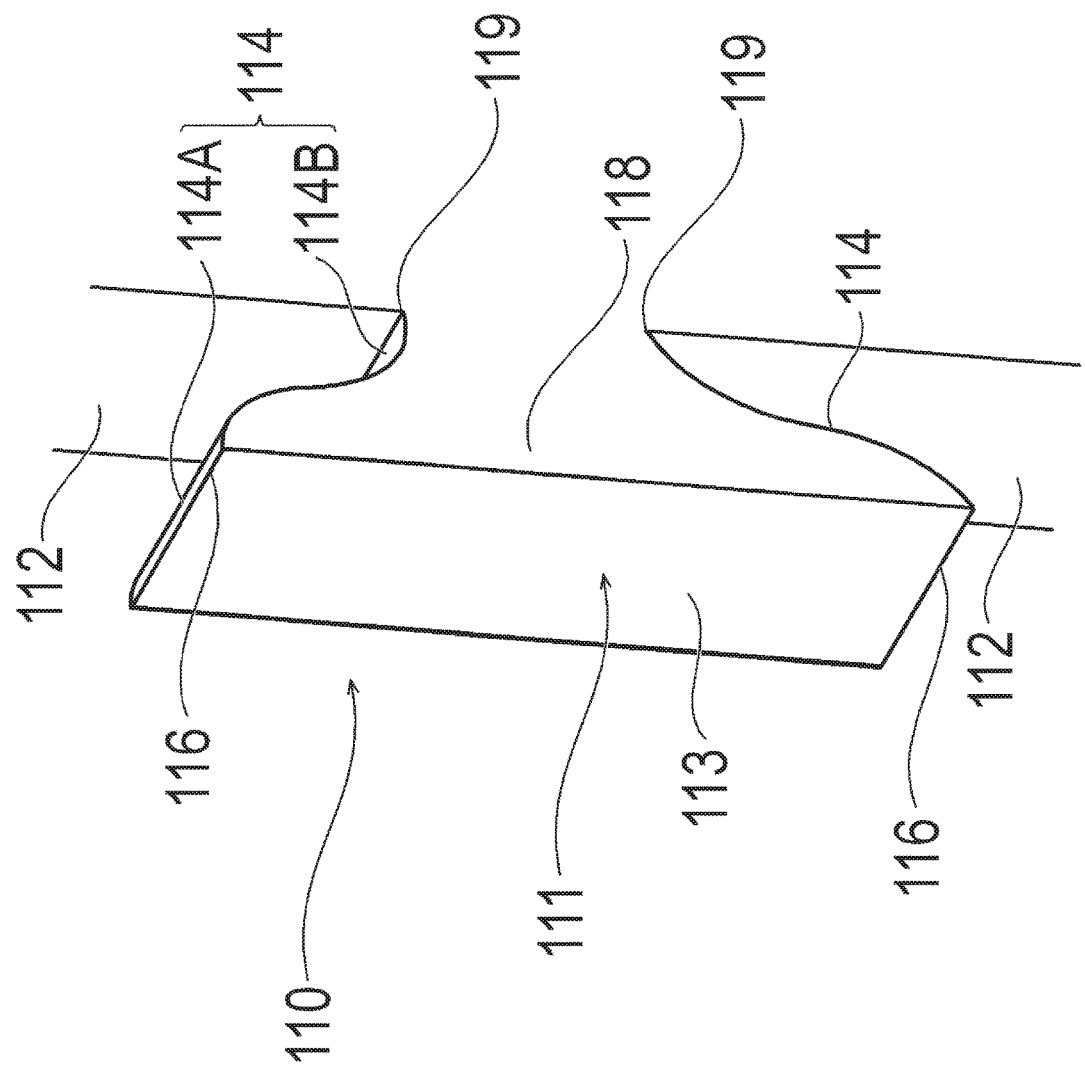
FIG. 6 is a perspective view showing a second opposing surface.

Hereinafter, embodiments of the present disclosure will be described with reference to the drawings. Note that, dimension ratios in the drawings may be exaggerated and may differ from the actual ratios for convenience of description.

A medical elongated body 10 according to the present embodiment is inserted into an artery, and is used for an atherectomy for cutting and removing a lesion area such as a calcified plaque. In the present specification, a side of the device inserted into a blood vessel is referred to as a "distal side", and a hand-side to be operated is referred to as a "proximal side".

In accordance with an exemplary embodiment, the medical elongated body 10 can include, as shown in FIG. 1, an elongated shaft portion 20 which is rotationally driven, an outer sheath 30 which can accommodate the shaft portion 20, and a cutting portion 40 which is rotated by the shaft portion 20. The medical elongated body 10 further includes a rotationally driving portion 50 which has a driving source (for example, motor) for rotating the shaft portion 20 and a hub 60 which is provided at a proximal side end portion of the shaft portion 20. In accordance with an exemplary embodiment, diamond particles (abrasive material) are attached to the outer surface of the cutting portion 40 so that the lesion area can be cut. A blade surface may be provided at the distal end of the cutting portion 40 in the circumferential direction. Note that, the configuration of the cutting portion 40 is not particularly limited as long as the lesion area can be cut.

The shaft portion 20 can include an outer tube shaft 21 rotationally driven by the rotationally driving portion 50 and an inner tube shaft 22 disposed on the inner side of the outer tube shaft 21 and to which the hub 60 is fixed at the proximal portion. The outer tube shaft 21 includes a tube shaped body 70 in which a spiral slit 71 is provided to transmit rotationally driving force while obtaining flexibility.

The tube shaped body 70 has, as shown in FIGS. 2 to 6, the slit 71 disposed along a passage extending in a spiral shape while meandering (repeatedly bending). The tube shaped body 70 includes, a flexible portion 72 on a distal side in which the slit 71 is provided and a high rigidity portion 73 on a proximal side in which the slit 71 is not provided. The slit 71 is formed by spiral slit processing using a technique generally performed, for example, such as laser processing.

In accordance with an exemplary embodiment, the flexible portion 72 is provided with the slit 71 at a predetermined pitch L1. The slit 71 is a linear slit penetrating from an outer peripheral surface to an inner peripheral surface of the tube shaped body 70, and is continuous so as to draw a spiral while curving so as to form a convex portion and a concave portion to be described later in the tube shaped body 70. The pitch L1 means a distance that the slit 71 moves in an axial direction X of the tube shaped body 70 by winding around 360 degrees in a circumferential direction Y of the tube shaped body 70. The flexible portion 72 of the tube shaped body 70 has a flexible structure easily bendable due to the reduced flexural rigidity by providing the slit 71. Note that, the tube shaped body 70 may be configured with a multiple spiral structure by providing a plurality of spiral slits. The flexible portion 72 has one belt portion 210, which is a belt shape plate member between the slits 71 aligned in the axial direction X (see FIG. 7). The belt portion 210 draws a spiral and constitutes the flexible portion 72. Note that, in a case where the tube shaped body 70 has the multiple spiral structure, the flexible portion is configured of a plurality of belt portions.

In accordance with an exemplary embodiment, the slit 71 is configured by a pair of a first opposing surface 100 and a second opposing surface 110 disposed opposite to each other. The first opposing surface 100 can be the proximal side, the distal side, or the circumferential direction side. The second opposing surface 110 is opposite to the first opposing surface 100. In accordance with an exemplary embodiment, the first opposing surface 100 is an end surface on the distal side of the spiral structure body located between two slits 71 aligned in the axial direction. The first opposing surface 100 is a surface connecting the inner peripheral surface and the outer peripheral surface of the tube shaped body 70. The first opposing surface 100 extends in the circumferential direction along the spiral structure body located between the slits 71. The second opposing surface 110 is an end surface on the proximal side of the spiral structure body located between two slits 71 aligned in the axial direction. The second opposing surface 110 is a surface connecting the inner peripheral surface and the outer peripheral surface of the tube shaped body 70. The second opposing surface 110 extends in the circumferential direction along the spiral structure body located between the slits 71. The first opposing surface 100 and the second opposing surface 110 are adjacent (opposite) to each other interposing the slit 71 between the first opposing surface 100 and the second opposing surface 110. The first opposing surface 100 has a plurality of first convex portions 101 (convex portions) protruding toward the proximal side. The second opposing surface 110 has a plurality of second convex portions 111 (convex portions) protruding toward the distal side.

The first opposing surface 100 on the distal side has a plurality of first concave portions 102 (concave portions) into which the second convex portions 111 enter between the first convex portions 101 adjacent to each other in the circumferential direction. The second opposing surface 110 on the proximal side has a plurality of second concave portions 112 (concave portions) into which the first convex portions 101 enter between the plurality of second convex portions 111. In accordance with an exemplary embodiment, the first convex portions 101 are caught (i.e., held) in the second concave portions 112 so that the relative movement in the axial direction X and the circumferential direction Y with respect to the second concave portions 112 is restricted. The second convex portions 111 are caught (i.e., held) in the first concave portions 102 so that the relative movement in the axial direction X and the circumferential direction Y with respect to the first concave portions 102 is restricted. In accordance with an exemplary embodiment, the first convex portions 101 and the second convex portions 111 are disposed every 90 degrees in the circumferential direction. Note that, the interval at which the first convex portions 101 and the second convex portions 111 are disposed is not limited to 90 degrees, and for example, may be randomly disposed.

In accordance with an exemplary embodiment, the slit 71 can be located on two parallel first spirals 81 or second spirals 82 by drawing a spiral while bending in the tube shaped body 70. Top portions 101A on the protruding side (proximal side) of the first convex portions 101 are located on the first spiral 81. Top portions 111A on the protruding side (distal side) of the second convex portions 111 are located on the second spiral 82. In accordance with an exemplary embodiment, by locating, the slit 71 on the plurality of spirals (first spiral 81 or second spiral 82), the tube shaped body 70 easily bends with each of the spirals as a joint, and becomes relatively flexible.

In accordance with an exemplary embodiment, each of the first convex portions 101 has a first wide portion 108 (wide portion) having a width widening in the circumferential direction Y on the protruding side (proximal side). Each of the first convex portions 101 has a linearly extending first plane portion 103 (plane portion) constituting an end surface on the protruding side and a first side portion 104 (side portion) extending from both circumferential end portions of the first plane portion 103 toward the distal side. The first side portion 104 has a first curved surface 104A located on the protruding side, a second curved surface 104B positioned on the base portion side (opposite side of protruding side). The first curved surface 104A has a convex shape, and the second curved surface 104B has a concave shape. That is, the first curved surface 104A and the second curved surface 104B are curved in the opposite direction. Accordingly, in a developed view of the tube shaped body 70 in the circumferential direction (hereinafter, referred to as circumferential developed view), an inflection point 105 is provided between the first curved surface 104A and the second curved surface 104B. Note that, the "inflection point" is a point at which a bending direction changes. The first plane portion 103 of the first opposing surface 100 is parallel to the opposing second opposing surface 110, but may not be parallel.

In the circumferential developed view, a tangentially discontinuous corner portion 106 is provided between the first plane portion 103 and the first side portion 104. Note that, tangential discontinuity means that in a case where two lines are connected at a connection point, tangents of respective lines at the connection point are different. In accordance with an exemplary embodiment, a tangent means an extremely straight line when a moving point approaches a fixed point when there is a straight line connecting the fixed point and the moving point on the curved line (or straight line). Note that, each of two connected lines may be a straight line or a curved line. A tangent of the straight line coincides with the straight line. In accordance with an exemplary embodiment, the corner portion 106 is relatively sharp because of the tangential discontinuity (i.e., each of the surfaces share a common endpoint). Note that, the tangentially discontinuous corner portion 106 may have a certain degree of curvature radius due to a processing accuracy and the like. In accordance with an exemplary embodiment, the allowable curvature radius of the corner portion 106 is preferably 1.0 mm or less, more preferably 0.5 mm or less, and further preferably 0.05 mm or less. The smaller the curvature radius of the corner portion 106, the higher the effect of the engagement by the corner portion 106 as described later. In the circumferential developed view, it is preferable that an angle α1 of the corner portion 106 is larger than an angle β1 formed between a straight line N1 connecting the corner portion 106 and the inflection point 105 and the first plane portion 103, but is not limited to the angle α1 of the corner portion 106 being larger than the angle β1 formed between the straight line N1 connecting the corner portion 106 and the inflection point 105 and the first plane portion 103. Note that, the angle α1 of the corner portion 106 is an angle formed between a tangent at the corner portion 106 of the first curved surface 104A and the first plane portion 103. Therefore, it is preferable that the tangent at the corner portion 106 of the first curved surface 104A does not coincide with the first plane portion 103. Since the angle α1 is larger than the angle β1, the first side portion 104 has a convex shape toward sideways (i.e., towards the circumferential direction at an angle towards the distal end) at the first curved surface 104A on the protruding side. In accordance with an exemplary embodiment, the angle α1 of the corner portion 106 is preferably 90 degrees or less. If the angle α1 of the corner portion 106 is 90 degrees or less, rotation force acts on the tube shaped body 70, so that the corner portion 106 can be engaged with the second concave portions 112, and the torque transmission capability is relatively high.

In accordance with an exemplary embodiment, the first curved surface 104A and the second curved surface 104B are in a point symmetric shape (i.e., each part of the first curved surface 104A has a matching or corresponding part of the second curved surface 104B) with respect to the inflection point 105 in the circumferential developed view.

Note that, in accordance with an exemplary embodiment, the first curved surface 104A and the second curved surface 104B may not be in a point symmetric shape. For example, in accordance with an exemplary embodiment, a distance A1 from an intersection 107 of the straight line N1 vertically extending from the first inflection point 105 to the first plane portion 103 and the first plane portion 103 to the corner portion 106 is longer than the shortest distance A2 from the inflection point 105 to the first plane portion 103. Thereby, a relatively long distance from the inflection point 105 to the corner portion 106 can be secured, and each of the first convex portions 101 is deeply caught (i.e., held) in the second opposing surface 110 so that it is possible to suppress the occurrence of both elongation in the axial direction X and twisting which causes deterioration in the torque transmission performance. Moreover, when the distance A1 is longer than the distance A2, the first wide portion 108 becomes longer in the circumferential direction Y, but the distance A1 is along the rotation direction. Accordingly, the first wide portion 108 is less susceptible to the large force in the rotation direction, and the breakage of the first wide portion 108 and the tube shaped body 70 can be suppressed.

In accordance with an exemplary embodiment, the second concave portions 112 have a structure that is separated from the first convex portions 101 by the width of the slit 71. Therefore, each of the second concave portions 112 has a corner 119 having the same angle with the angle α1 in the circumferential developed view so that the corner portion 106 of the first convex portions 101 can be fitted and engaged. The corner 119 can have tangential discontinuity. Note that, the tangentially discontinuous corner 119 may have a certain degree of curvature radius due to a processing accuracy and the like.

In accordance with an exemplary embodiment, in the circumferential developed view, two corner portions 106 located at both end portions of the first plane portion 103 are located at end of both sides of the first convex portions 101 having these two corner portions 106 in the circumferential direction Y. That is, each of the whole (i.e., entirety of the) first convex portions 101 is located between the two corner portions 106 in the circumferential direction Y.

In accordance with an exemplary embodiment, each of the second convex portions 111 has a second wide portion 118 (wide portion) having a width widening in the circumferential direction Y on the protruding side (distal side). Each of the second convex portions 111 has a linearly extending second plane portion 113 (plane portion) constituting an end surface on the protruding side and a second side portion L (side portion) extending from both circumferential end portions of the second plane portion 113 toward the distal side. The second side portion 114 has a first curved surface 114A located on the protruding side and a second curved surface 114B located on the base portion side (opposite side of protruding side). The first curved surface 114A has a convex shape, and the second curved surface 114B has a concave shape. That is, for example, the first curved surface 114A and the second curved surface 114B are curved in the opposite direction. Accordingly, in the circumferential developed view, an inflection point 115 is provided between the first curved surface 114A and the second curved surface 114B. The second plane portion 113 of the second opposing surface 110 is parallel to the opposing first opposing surface 100, but may not be parallel.

In the circumferential developed view, a tangentially discontinuous corner portion 116 is provided between the second plane portion 113 and the second side portion 114. The corner portion 116 is sharp because of the tangential discontinuity. Note that, the tangentially discontinuous corner portion 116 may have a certain degree of curvature radius due to a processing accuracy and the like. In accordance with an exemplary embodiment, for example, the curvature radius of the corner portion 116 is preferably 1.0 mm or less, more preferably 0.5 mm or less, and further preferably 0.05 mm or less. The smaller the curvature radius of the corner portion 116, the higher the effect of the engagement by the corner portion 116 as described later. In the circumferential developed view, it is preferable that an angle α2 of the corner portion 116 is larger than an angle β2 formed between a straight line N2 connecting the corner portion 116 and the inflection point 115 and the second plane portion 113, but is not limited thereto. Note that, the angle α2 of the corner portion 116 is an angle formed between a tangent at the corner portion 116 of the second curved surface 114A and the second plane portion 113. Therefore, it is preferable that the tangent at the corner portion 116 of the second curved surface 114A does not coincide with the second plane portion 113. Since the angle α2 is larger than the angle β2, the second side portion 114 has a convex shape toward sideways at the second curved surface 114A on the protruding side. In accordance with an exemplary embodiment, for example, the angle α2 of the corner portion 116 is preferably 90 degrees or less. If the angle α2 of the corner portion 116 is 90 degrees or less, rotation force acts on the tube shaped body 70, so that the corner portion 116 can be well engaged with the first concave portions 102, and the torque transmission capability is relatively high.

In accordance with an exemplary embodiment, the first curved surface 114A and the second curved surface 114B are in a point symmetric shape (i.e., each part of the first curved surface 114A has a matching or corresponding part of the second curved surface 114B) with respect to the inflection point 115 in the circumferential developed view. Note that, the first curved surface 114A and the second curved surface 114B may not be in a point symmetric shape. In accordance with an exemplary embodiment, a distance A3 from an intersection 117 of the straight line N2 vertically extending from the second the inflection point 115 to the second plane portion 113 and the second plane portion 113 to the corner portion 116 is longer than the shortest distance A4 from the inflection point 115 to the second plane portion 113. Thereby, a long distance from the inflection point 115 to the corner portion 116 can be secured, and a first convex portion 111 is deeply caught (i.e., held) in the first opposing surface 100, so that it is possible to suppress the occurrence of both elongation in the axial direction X and twisting which causes deterioration in the torque transmission performance. Moreover, when the distance A3 is longer than the distance A4, the second wide portion 118 becomes longer in the circumferential direction Y, but the distance A3 is along the rotation direction. Accordingly, the second wide portion 118 is less susceptible to the large force in the rotation direction, and the breakage of the second wide portion 108 and the tube shaped body 70 can be suppressed.

In accordance with an exemplary embodiment, the first concave portions 102 have a structure that is separated from the second convex portions 111 by the width of the slit 71. Therefore, each of the first concave portions 102 has a corner 109 having the same angle with the angle α2 in the circumferential developed view so that the corner portion 116 of the second convex portions 111 can be fitted and engaged. The corner 109 has tangential discontinuity (i.e., each of the surfaces share a common endpoint). Note that, the tangentially discontinuous corner 109 may have a certain degree of curvature radius due to a processing accuracy and the like.

In accordance with an exemplary embodiment, in the circumferential developed view, two corner portions 116 located at both end portions of the second plane portion 113 are located at end of both sides of the second convex portions 111 having these two corner portions 116 in the circumferential direction Y. That is, each of the whole (i.e., entirety of the) second convex portions 111 is located between the two corner portions 116 in the circumferential direction Y.

In accordance with an exemplary embodiment, it can be preferable that the distance L2 which is the protruding length of the first convex portions 101 and the second convex portions 111 in the axial direction X is equal to or less than half the pitch L1 of the first spiral 81 (or second spiral 82), but are not limited thereto. For example, if the distance L2 is equal to or less than half the pitch L1, the possibility of occurrence of a site where the interval between two slits 71 aligned in the axial direction X becomes excessively narrow can be suppressed, and the width of the material between the two slits 71 can be maintained. Thereby, the appropriate strength of the medical elongated body 10 can be secured in the tube shaped body 70. In accordance with an exemplary embodiment, it can be preferable that the distance L2 is not excessively short and a certain length is secured so that the strength of the first convex portions 101 and the second convex portions 111 can be secured. The pitch L1 is not particularly limited, but is, for example, 0.1 mm to 30 mm. The distance L2 is not particularly limited, but is, for example, 0.05 mm to 18 mm.

The first convex portions 101 on the first opposing surface 100 on the distal side and the second convex portions 111 on the second opposing surface 110 on the proximal side adjacent to each other in the circumferential direction Y are disposed in pairs. A convex portion group 120 configured of the adjacent first convex portions 101 and second convex portions 111 is provided by a predetermined interval in the circumferential direction Y.

In accordance with an exemplary embodiment, the adjacent first convex portions 101 and second convex portions 111 of each convex portion group 120 are, in a developed view, point symmetric with respect to a point (intermediate point between adjacent inflection point 105 and inflection point 115) located between the first convex portions 101 and the second convex portions 111 of each convex portion group 120. That is, the first convex portions 101 and the second convex portions 111 have the same size and shape, but differ only in orientation. Therefore, the second convex portions 111 have configuration structure symmetric with the first convex portions 101. Note that, having the same size means that the dimensions are the same. Moreover, having the same shape means that the shapes are in a similarity relationship in a developed view.

In accordance with an exemplary embodiment, the convex portion group 120 is located, for example, every 90 degrees in the circumferential direction Y. Accordingly, the convex portion group 120 is disposed side by side in the axial direction X by winding the slit 71. Note that, the convex portion group 120 may not be disposed every 90 degrees in the circumferential direction Y. Therefore, the convex portion group 120 may not be disposed side by side in the axial direction X.

The tube shaped body 70 material is preferably a material with relatively high rigidity, and for example, metals such as Ni—Ti, brass, SUS, and aluminum are preferably used. Note that, as long as the tube shaped body 70 material has relatively high rigidity, the material of the tube shaped body 70 is not particularly limited, and for example, it may be a resin such as polyimide, vinyl chloride, and polycarbonate.

The dimension of the tube shaped body 70 is not particularly limited. For example, the tube shaped body 70 can have an outer diameter of approximately 0.5 mm to 3.5 mm, a thickness of approximately 10 µm to 170 µm, and a length of approximately 1,100 mm to 1,400 mm.

The width (separated distance between first opposing surface 100 and second opposing surface 110) of a gap of the slit 71 is not particularly limited, but is, for example, approximately 0.01 mm to 0.05 mm.

Next, a method of using the medical elongated body 10 according to the present embodiment will be described with a case of cutting a calcified lesion area in the artery as an example.

When using the medical elongated body 10 of the present embodiment, a guide wire (not shown) is inserted into the blood vessel, and the medical elongated body 10 reaches the proximal side of the calcified lesion area with the guide wire as a guide while bending and rotating the medical elongated body 10.

Next, when the shaft portion 20 is rotated by the rotationally driving portion 50 in a state where the cutting portion 40 is advanced to the vicinity of the lesion area, the cutting portion 40 also rotates accordingly. When the cutting portion 40 is moved in the blood vessel in this state, the cutting portion 40 comes into contact with the lesion area, and the cutting portion 40 cuts the lesion area in the blood vessel. Although the rotation of the cutting portion 40 is a continuous rotation in one direction, it may be rotated in the reverse direction, if necessary.

In accordance with an exemplary embodiment, the cut lesion area is collected in a separately attached filter in the blood vessel. The lesion area collected by the filter can be discharged to the outside of the blood vessel with the filter. Alternatively, the cut lesion area can be aspirated and discharged to the outside of the blood vessel. After the lesion area is cut, the rotation stops. Thereafter, the medical elongated body 10 is removed from the blood vessel and the procedure is completed.

As described above, the medical elongated body 10 according to the embodiment is the medical elongated body 10 including the tube shaped body 70, the tube shaped body 70 has the slit 71 extending in a spiral shape while meandering, the slit 71 forms a pair of the first opposing surface 100 and the second opposing surface 110, the first opposing surface 100 forms the first convex portions 101, the first convex portions 101 has the first wide portion 108 (wide portion) having a width widening in the circumferential direction Y of the tube shaped body 70, the second opposing surface 110 forms the second concave portions 112 (concave portions) which surround and accommodate the first wide portion 108, each of the first convex portions 101 has the first plane portion 103 (plane portion) and two first side portions 104 (side portions) connected to both end portions in the circumferential direction Y of the first plane portion 103, and, in the circumferential developed view, the first side portion 104 and the first plane portion 103 have tangent discontinuity.

In the medical elongated body 10 configured as described above, the second concave portions 112 surround and accommodate the first wide portion 108, and the first convex portions 101 are caught in the second opposing surface 110. Therefore, the elongation in the axial direction X and the occurrence of twisting which causes deterioration in the torque transmission performance in the medical elongated body 10 can be suppressed. Moreover, the first side portion 104 and the first plane portion 103 have tangent discontinuity in the circumferential developed view. Accordingly, when the torque acts on the medical elongated body 10, the pair of the first opposing surface 100 and the second opposing surface 110 are engaged. Thereby, the first opposing surface 100 and the second opposing surface 110 are in an interlocked state, and the torque transmission capability improves. Note that, herein, the effect of the configuration in which the first convex portions 101 of the first opposing surface 100 on the distal side are surrounded and accommodated in the second concave portions 112 of the second opposing surface 110 on the proximal side is described, but the same effect can be obtained from the configuration in which the second convex portions 111 of the second opposing surface 110 on the proximal side are surrounded and accommodated in the first concave portions 102 of the first opposing surface 100 on the distal side. In accordance with an exemplary embodiment, by exhibiting the effect on both sides of the paired first opposing surface 100 and the second opposing surface 110, a better effect can be synergistically obtained. For example, in a case where the cutting portion 40 receiving the cutting resistance receives excessive cutting resistance by improving the torque transmission capability, the resistance can be effectively transmitted to the proximal side and the rotation of the medical elongated body 10 can be stopped.

Moreover, at least one of the side portions 104 has a curved surface. Accordingly, the contact area between the pair of the first opposing surface 100 and the second opposing surface 110 increases and comes into contact with each other relatively smoothly, and the torque can be smoothly transmitted in the bent state. In particular, the tube shaped body 70 is a member for rotating and transmitting the rotation force in order to cut a hard lesion area. Therefore, it is desirable that the tube shaped body 70 can smoothly and efficiently transmit the torque in a state where the tube shaped body 70 is bent.

In accordance with an exemplary embodiment, the first curved surface 104A of the side portion 104 is connected to the plane portion 103. Accordingly, the first curved surface 104A is located near a position (corner portion 106 and corner 119) where the first opposing surface 100 and the second opposing surface 110 are engaged. Thereby, the pair of the first opposing surface 100 and the second opposing surface 110 comes into contact with each other relatively smoothly. Accordingly, the tube shaped body 70 can transmit torque even in the bent state relatively smoothly.

In accordance with an exemplary embodiment, the first side portion 104 and the first plane portion 103 intersect at the corner portion 106 in a tangential discontinuity in the circumferential developed view. Accordingly, when the torque acts on the medical elongated body 10, the pair of the first opposing surface 100 and the second opposing surface 110 can be engaged at the tangentially discontinuous corner portion 106. Thereby, the first opposing surface 100 and the second opposing surface 110 are in an interlocked state, and the torque transmission capability improves.

In accordance with an exemplary embodiment, the first side portion 104 (side portion) has the first curved surface 104A and the second curved surface 104B having different bending directions in the circumferential developed view. Thereby, since the first side portion 104 can maintain the relative smoothness while securing the length by bending, the pair of the first opposing surface 100 and the second opposing surface 110 can be brought into contact with each other in the increased contact area in a relatively smooth manner. Accordingly, the medical elongated body 10 can smoothly transmit torque even in the bent state, and the transmission capability improves.

In accordance with an exemplary embodiment, the first curved surface 104A and the second curved surface 104B are in a point symmetric shape in the circumferential developed view. Thereby, in the medical elongated body 10, the difference in the torque transmission performance depending on the rotation direction can be reduced, and relatively high smooth torque transmission performance can be exhibited in any rotation directions, so that the operability of the medical elongated body 10 is improved.

In accordance with an exemplary embodiment, in the circumferential developed view, the first side portion 104 (side portion) has the inflection point 105 between the first curved surface 104A and the second curved surface 104B. Thereby, the bending direction naturally changes at the inflection point 105 while securing the length by bending the first side portion 104. Accordingly, the medical elongated body 10 bends naturally so that unnecessary force does not act, and the torque can be transmitted even in the bent state.

In accordance with an exemplary embodiment, in the circumferential developed view, the angle $\alpha 1$ of the corner portion 106 is larger than the angle $\beta 1$ between the straight line N1 connecting the corner portion 106 and the inflection point 105 and the first plane portion 103 (plane portion). Thereby, since the corner portion 106 does not become relatively too sharp, the strength can be secured and the safety of medical elongated body 10 can be relatively high.

In accordance with an exemplary embodiment, in the circumferential developed view, the distance A1 from the intersection 107 of the straight line vertically extending from the inflection point 105 to the first plane portion 103 (plane portion) and the first plane portion 103 to the corner portion 106 is longer than the distance A2 from the inflection point 105 to the first plane portion 103. Thereby, it is possible to secure a long distance from the inflection point 105 to the corner portion 106, and each of the first convex portions 101 is deeply caught (i.e., held) in the second opposing surface 110 so that it is possible to suppress the occurrence of both elongation in the axial direction X and twisting which can cause deterioration in the torque transmission performance.

In accordance with an exemplary embodiment, the first convex portions 101 and the second convex portions 111 adjacent to each other in the circumferential direction Y are in a point symmetric shape in the circumferential developed view. Thereby, since the rotation force of the medical elongated body 10 is dispersed in the first convex portions 101 and the second convex portions 111 in a well-balanced manner, the torque transmission performance can be improved, and the occurrence of the breakage of the medical elongated body 10 can be suppressed.

In accordance with an exemplary embodiment, in the circumferential developed view, the first plane portion 103 and the second plane portion 113 are parallel. Thereby, since the tube shaped body 70 easily bends like a joint at both the position of the first plane portion 103 and the position of the second plane portion 113 and bends naturally because it is parallel and unnecessary force does not act, and thereby the flexibility increases and the operability improves.

In accordance with an exemplary embodiment, in the circumferential developed view, the corner portion 106 intersecting with the first side portion 104 is provided at both end portions of the first plane portion 103 and the two corner portions 106 are located at end of both sides of the first convex portions 101 having these two corner portions 106 in the circumferential direction Y. That is, each of the whole (i.e., entirety of the) first convex portions 101 is located between the two corner portions 106 in the circumferential direction Y. Thereby, the pair of the first opposing surface 100 and the second opposing surface 110 does not depend on the direction of the torque acting on the medical elongated body 10 and are engaged with each other. Accordingly, the first opposing surface 100 and the second opposing surface 110 are in an interlocked state, and the torque transmission capability of the medical elongated body 10 improves.

Figure 7:
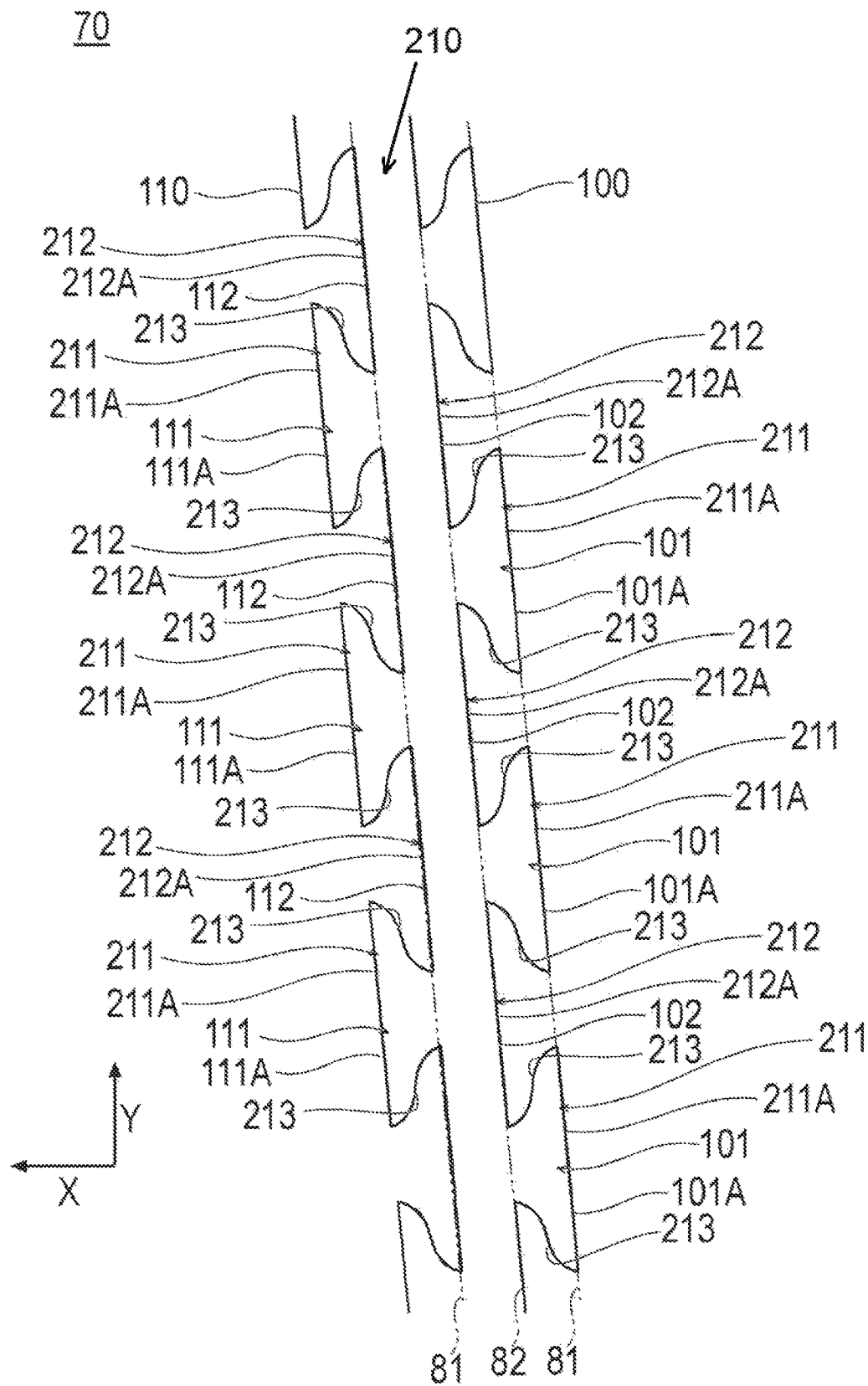
FIG. 7 is a developed view showing a portion of a belt portion of the tube shaped body continuously in the circumferential direction.

In accordance with an exemplary embodiment, in the medical elongated body 10 according to the embodiment, as shown in FIG. 7, the medical elongated body 10 has the tube shaped body 70 in which the belt portion 210 which is a plate member extending in a spiral shape is provided. In accordance with an exemplary embodiment, the belt portion 210 has the inner peripheral surface located on the inner surface of the tube shaped body 70, the outer peripheral surface located on the outer surface of the tube shaped body 70, and two side surfaces interlocking the inner peripheral surface and the outer peripheral surface, the side surfaces have a mountain shape 211 and a valley shape 212, the mountain shape 211 and the valley shape 212 have a width widening on a top surface 211A side of the mountain and on a bottom 212A side of the valley in the extending direction of the belt portion 210, and a connection surface 213 connecting the top surface 211A of the mountain and the bottom 212A of the valley of the mountain shape 211 and the valley shape 212 has an S shape in the circumferential developed view.

In the medical elongated body 10 configured as described above, since the valley shape 212 is surrounding and accommodating the mountain shape 211 having wide width on the top surface 211A side, the mountain shape 211 is caught (i.e., held) in both the axial direction X and the circumferential direction Y with respect to the valley shape 212. Therefore, the elongation in the axial direction X and the occurrence of twisting which causes deterioration in the torque transmission performance in the medical elongated body 10 can be suppressed. Moreover, the connection surface 213 connecting the top surface 211A and the bottom 212A has an S shape in the circumferential developed view. Accordingly, the mountain shape 211 and the valley shape 212 which come into contact with each other as a pair are smoothly brought into contact with each other in the increased contact area, and can smoothly transmit torque even in the bent state. Thereby, the mountain shape 211 and the valley shape 212 are in an interlocked state, and the torque transmission capability of the medical elongated body 10 can be improved. Moreover, in a case where the cutting portion 40 receiving the cutting resistance receives excessive cutting resistance by improving the torque transmission capability, the resistance is effectively transmitted to the proximal side and the rotation of the medical elongated body 10 can be stopped.

In accordance with an exemplary embodiment, the mountain shape 211 and the valley shape 212 are fitted to each other by disposing the belt portion 210 in a spiral shape. Thereby, the mountain shape 211 is more likely to be caught (i.e., held) in the valley shape 212 accommodating the mountain shape 211 in both directions of the axial direction X and the circumferential direction Y. Accordingly, in the medical elongated body 10, the elongation in the axial direction X and the occurrence of twisting are suppressed and the torque transmission performance is improved.

In accordance with an exemplary embodiment, the mountain shape 211 and the valley shape 212 have substantially the same shape. Accordingly, the mountain shape 211 can be fitted to the valley shape 212. Therefore, the mountain shape 211 and the valley shape 212 are easily caught (i.e., held) in both directions of the axial direction X and the circumferential direction Y. Accordingly, in the medical elongated body 10, the elongation in the axial direction X and the occurrence of twisting are suppressed and the torque transmission performance can be improved.

Note that, the present disclosure is not limited only to the embodiments described above, and various modifications are possible by those skilled in the art within the technical idea of the present disclosure. For example, as shown in FIG. 8, a tube shaped body 130 of a first modification example may be provided with a linear intermediate plane portion 133 between the first curved surface 104A and the second curved surface 104B provided on the side portions of a first convex portion 131, in the circumferential developed view. That is, a site where the bending direction changes may not be a point (inflection point) but linear. Note that, the same reference numerals are attached to the parts having similar functions as those of above-described embodiment, and the description of the same reference numerals having similar functions will be omitted. The intermediate plane portion 133 is parallel to the first spiral 81 and the second spiral 82. In a medical elongated body having such a tube shaped body 130, the flexibility against bending is not disturbed by the intermediate plane portion 133, and the first convex portion 131 is deeply caught (i.e., held) in a second concave portion 132, so that it is possible to effectively suppress the elongation and the twisting in the axial direction X. Moreover, since the tube shaped body 130 is easily bent in the intermediate plane portion 133 in addition to the first plane portion 103 and the second plane portion 113, the flexibility of the medical elongated body 10 improves.

In accordance with an exemplary embodiment, in the circumferential developed view, a spiral on which a plurality of the intermediate plane portions 133 are aligned is disposed at a position different from the first spiral 81 on which the first plane portions 103 are aligned and the second spiral 82 on which the second plane portion 113 are aligned, and is parallel. Thereby, the tube shaped body 130 easily bends like a joint at the position of the first spiral 81, the position of the second spiral 82, and the position of the spiral on which the intermediate plane portions 133 are aligned, and thereby the flexibility of the medical elongated body 10 increases. Note that, the intermediate plane portion 133 may not be parallel to the first spiral 81 and the second spiral 82.

In accordance with an exemplary embodiment, as shown in FIG. 9, a tube shaped body 140 as a second modification example is provided with a first curved surface 142A and a second curved surface 142B provided on a first side portion 142 of a first convex portion 141. In the circumferential developed view, an inflection point (i.e., a point of a curve at which a change in the direction of curvature changes) 143 is provided between the first curved surface 142A and the second curved surface 142B. As shown in FIG. 9, the first curved surface 142A has a concave shape, and the second curved surface 142B has a convex shape. Even with such a configuration, in the medical elongated body, the side portion 142 and the first plane portion 103 intersect in a tangential discontinuity in the circumferential developed view. Accordingly, the first convex portion 141 and a second concave portion 145 are engaged with each other at a tangentially discontinuous corner portion 144 in a state where the torque is applied, the torque transmission capability improves.

In accordance with an exemplary embodiment, in the circumferential developed view, as shown in FIG. 10, in a tube shaped body 150 as a third modification example, an inflection point may not be provided on a first side portion 152 of the first convex portion 151. Even with such a configuration, in the medical elongated body, the side portion 152 and the first plane portion 103 intersect in a tangential discontinuity. Accordingly, the first convex portion 151 and a second concave portion 153 are engaged with each other at a tangentially discontinuous corner portion 154 in a state where the torque is applied, and the torque transmission capability improves.

In accordance with an exemplary embodiment, as shown in FIG. 11, in a tube shaped body 160 as a fourth modification example, the shapes of two first side portions 162 and 163 of a first convex portion 161 may be different from each other. Therefore, for example, the first convex portion 161 has a corner portion 164 only between the first side portion 162 and the first plane portion 103. In addition, a second convex portion 165 has a corner portion 167 only between a second side portion 166 and the second plane portion 113. Such a configuration can be advantageous in a case where the rotation direction is limited to one direction or in a case where the rotation use frequency is high in one direction. That is, in the case of rotating in a direction of high use frequency, the corner portion 164 of the first convex portion 161 is engaged with a second concave portion 168, or the corner portion 167 of the second convex portion 165 is engaged with a first concave portion 169, so that high torque transmission performance can be obtained. Furthermore, since the corner portion is not provided at a side portion on the other side, which is less engaged, the occurrence of the breakage can be suppressed and the safety of the medical elongated body 10 can be enhanced.

In accordance with an exemplary embodiment, as shown in FIG. 12, in a tube shaped body 170 as a fifth modification example, the pitch L1 of a slit 171 may change along the axial direction X. For example, by gradually narrowing the large pitch L1 of the slit 171 toward the distal side, it is possible to lower the flexural rigidity toward the distal side. Thereby, the tube shaped body 170 can secure sufficient pushing performance by a site on the proximal side having high flexural rigidity, can relatively easily pass through a curved site of a biological lumen by a flexible site on the distal side, and can obtain relatively high accessibility and operability at the same time. Moreover, the sizes and shapes of a first convex portion 172 and a second convex portion 173 may be different depending on the position in the axial direction X. For example, in the proximal portion having the large pitch L1, since there is a room in the pitch L1, the first convex portion 172 and the second convex portion 173 can be enlarged. In accordance with an exemplary embodiment, the pitch L1 of the slit 171 may change in an inclined manner. Thereby, the tube shaped body can obtain higher accessibility and operability, and the stress is not concentrated at one place, so that the occurrence of breakage and a kink of the medical elongated body 10 can be reduced. In accordance with an exemplary embodiment, the pitch L1 of the slit may be shorter toward the proximal side. In addition, the sizes and shapes of the first convex portion and the second convex portion may be smaller toward the proximal side.

In accordance with an exemplary embodiment, the medical elongated body 10 according to the present embodiment is a device for removing a lesion area such as a calcified plaque in the artery, but is not particularly limited as long as it is a medical elongated body. For example, in deep vein thrombosis, the medical elongated body may be a device inserted into the blood vessel and crushing a thrombus in an artery, catheters for other uses such as a microcatheter and an imaging catheter, a guide wire, and the like.

In accordance with an exemplary embodiment, the spiral direction of the slit of the tube shaped body is not limited. For example, the first convex portion and the second convex portion of the tube shaped body may not be disposed with regularity, or may be randomly disposed. Thereby, the anisotropy in the circumferential direction in the flexural rigidity of the tube shaped body can be reduced. Note that, by disposing the first convex portion and the second convex portion of the tube shaped body with regularity, it is possible to systematically adjust the bending direction.

In accordance with an exemplary embodiment, in the medical elongated body 10 according to the present embodiment, the outer tube shaft 21 is driven by the rotationally driving portion 50, but as shown in the sixth modification example in FIG. 13, the inner tube shaft 22 may be rotationally driven by the rotationally driving portion 50 instead of the outer tube shaft 21. In that case, the hub 60 is fixed to the proximal portion of the outer tube shaft 21.

In accordance with an exemplary embodiment, in a seventh modification example shown in FIG. 14A, both the inner tube shaft 22 and an outer tube shaft portion 21 may have the tube shaped body 70 in which the spiral slit 71 is provided. In accordance with an exemplary embodiment, in an eighth modification example shown in FIG. 14B, the slit 71 of the inner tube shaft 22 may overlap the slit 71 of the outer tube shaft 21 in the radial direction from the central axis of the inner tube shaft 22. The range where the slit 71 of the inner tube shaft 22 overlapping the slit 71 of the outer tube shaft 21 in the radial direction is, for example, a distal portion of the inner tube shaft 22 and the outer tube shaft 21.

Figure 15:
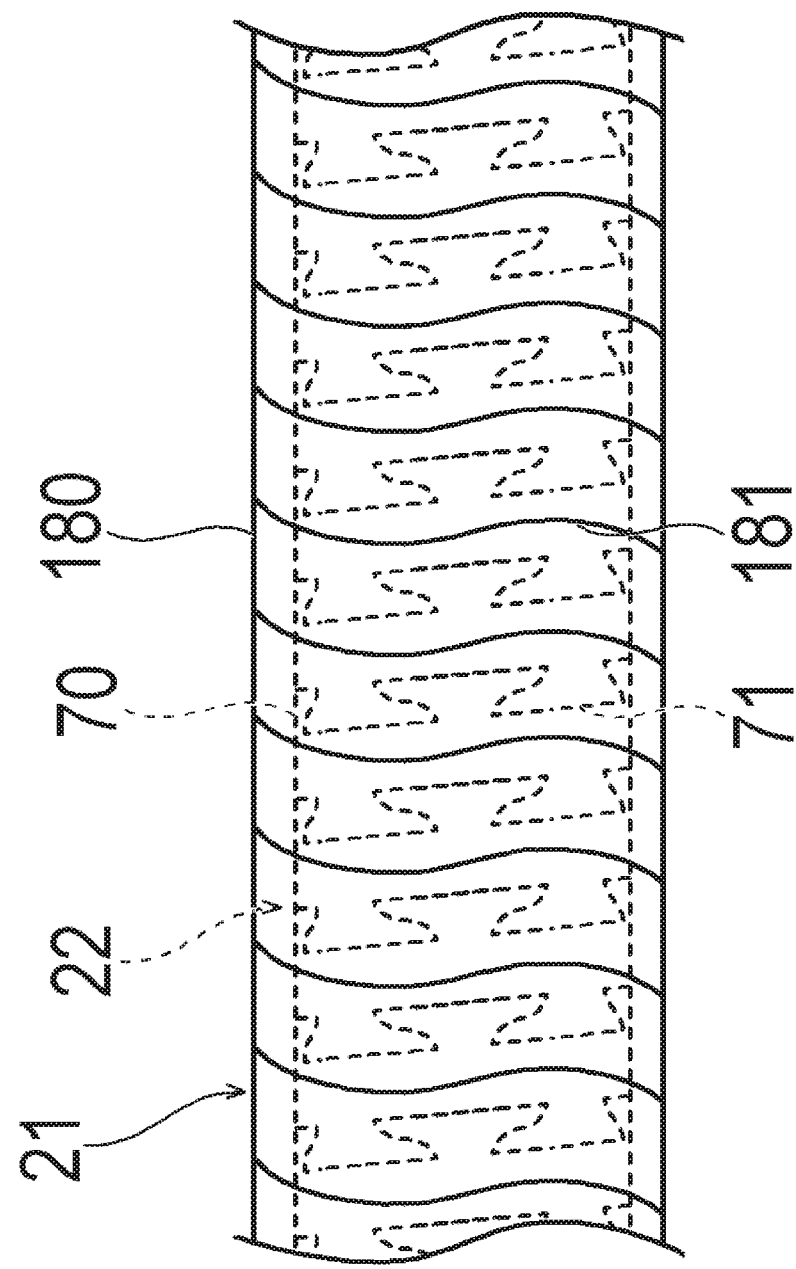
FIG. 15 is a plane view showing a portion of the shaft portion of a ninth modification example.

In accordance with an exemplary embodiment, in a ninth modification example shown in FIG. 15, the inner tube shaft 22 may include the tube shaped body 70 having the spiral slit 71, and the outer tube shaft 21 may include a tube shaped body 180 having a slit 181 having a different structure with the spiral slit 71. For example, the slit 181 draws a spiral while folding back in a curved shape in the circumferential developed view. Thereby, it is possible to make the outer tube shaft 21, which has larger diameter than the inner tube shaft 22 and is likely to have high rigidity, to be flexible. Therefore, it is possible to secure the flexibility and the pushing performance by the outer tube shaft 21 while suppressing the elongation in the axial direction X and the occurrence of twisting which causes deterioration in the torque transmission performance by the inner tube shaft 22. In this modification example, the inner tube shaft 22 which is capable of suppressing the elongation in the axial direction X and the occurrence of twisting which causes deterioration in the torque transmission performance by the provision of the slit 71 is rotationally driven, but is not limited thereto. Moreover, the slit 181 and the slit 71 are wound around in a reverse direction. Thereby, the strength is improved by different spirals reinforcing each other and the operability of the medical elongated body 10 is improved by reducing the anisotropy of the movement. Note that, the winding direction of the slit 71 and the slit 181 may be the same.

Figure 16:
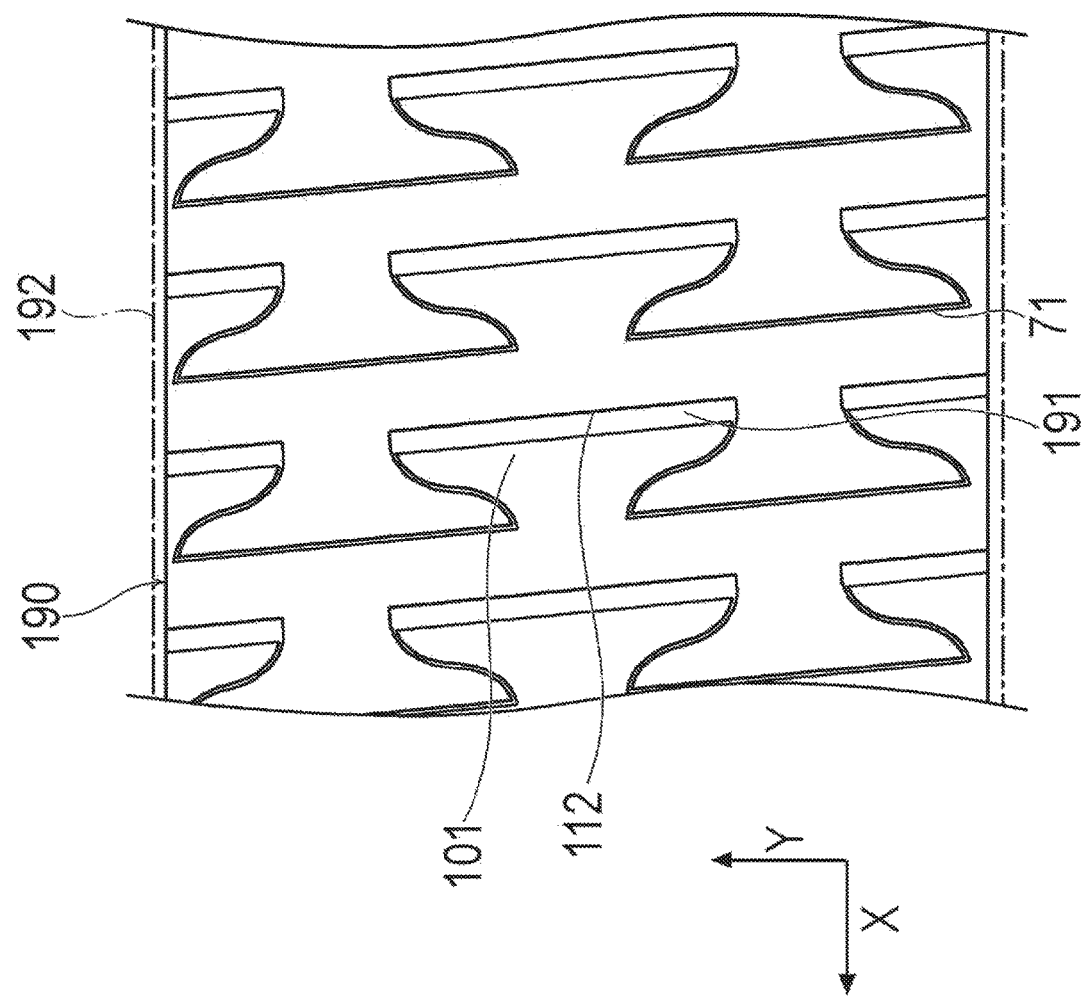
FIG. 16 is a plane view showing a portion of a tube shaped body of a tenth modification example.

In accordance with an exemplary embodiment, in a tenth modification example shown in FIG. 16, a tube shaped body 190 may include a space portion 191 having a gap of the slit 71 in which the interval is widening between the first convex portions 101 and the second concave portions 112. In the space portion 191, for example, a portion of a coating layer 192 covering the outer peripheral of a tube shaped body 191 can enter. Thereby, the coating layer 192 can be easily fixed to the tube shaped body 190. Moreover, when the shaft to which the tube shaped body 190 is applied is pushed into the tube shaped body 190, the first convex portions 101 enter the space portion 191, and the shaft tends to be a straight line. Accordingly, the shaft to which the tube shaped body 190 is applied becomes easy to apply a pushing force. Note that, the shape of the space portion 191 is not particularly limited, and may be, for example, a square shape, a triangular shape, a trapezoidal shape, a semicircular shape, or the like in the circumferential developed view.

Figure 17:
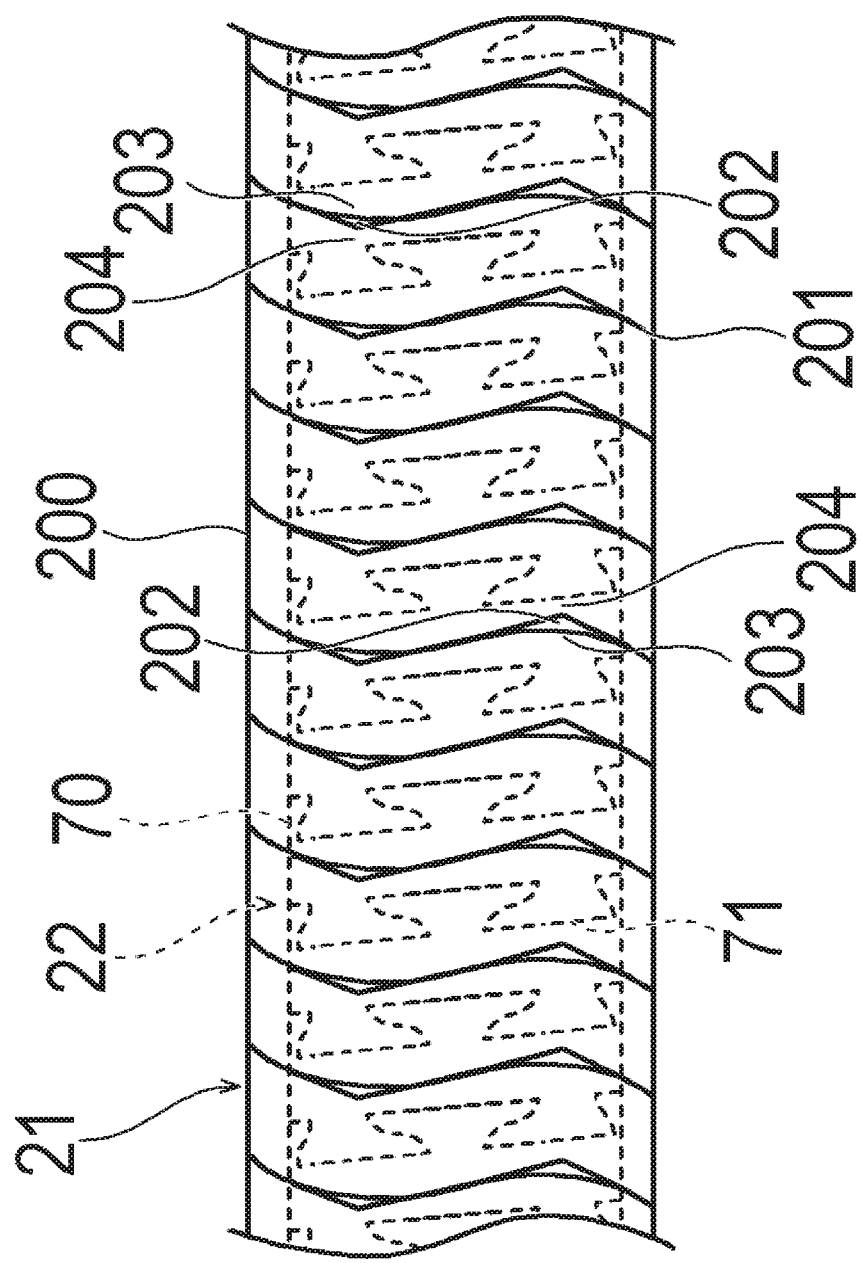
FIG. 17 is a plane view showing a portion of a shaft portion of an eleventh modification example.

In accordance with an exemplary embodiment, in an eleventh modification example shown in FIG. 17, the inner tube shaft 22 may include the tube shaped body 70 having the spiral slit 71 and the outer tube shaft 21 may include a tube shaped body 200 having a space portion 202 in which a slit 201 is provided. The slit 201 draws a spiral while folding back so as to include a convex portion 203 and a concave portion 204 in the circumferential developed view. In the circumferential developed view, the convex portion 203 is curved, and the concave portion 204 is bent while accommodating the convex portion 203. The space portion 202 is provided between the convex portion 203 and the concave portion 204. Thereby, it is possible to make the outer tube shaft 21, which has larger diameter than the inner tube shaft 22 and is likely to have a relative high rigidity, to be flexible. Therefore, it is possible to secure the flexibility and the pushing performance by the outer tube shaft 21 while suppressing the elongation in the axial direction X and the occurrence of twisting which causes deterioration in the torque transmission performance by the inner tube shaft 22. In this modification example, the inner tube shaft 22 which is capable of suppressing the elongation in the axial direction X and the occurrence of twisting which causes deterioration in the torque transmission performance by the provision of the slit 71 is rotationally driven, but is not limited thereto. In accordance with an exemplary embodiment, when the outer tube shaft 21 to which the tube shaped body 200 is applied is pushed into, the convex portion 203 enters the space portion 202, and the outer tube shaft 21 tends to be a straight line. Accordingly, the outer tube shaft 21 to which the tube shaped body 200 is applied becomes relatively easy to apply a pushing force. Note that, the shape of the space portion 202 is not particularly limited.

The detailed description above describes a medical elongated body to be inserted into a biological lumen. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body comprising:
a tube shaped body, the tube shaped body having a slit extending in a spiral shape while meandering, the slit being formed from a first opposing surface and a second opposing surface;
the first opposing surface forming a first convex portion, the first convex portion having a wide portion having a width widening in a circumferential direction of the tube shaped body;
the second opposing surface forming a concave portion that surrounds and accommodates the wide portion of the first convex portion, the first convex portion having a plane portion and two side portions, the two side portions being connected to both end portions of the plane portion of the first convex portion in the circumferential direction;
wherein the two side portions and the plane portion have tangential discontinuity in which each of the two sides portions have an endpoint with the plane portion and an angle between the each of the side portions and the plane portion is 90 degrees or less;
at least one of the two side portions having a curved surface, the curved surface having a first curved surface and a second curved surface, the first curved surface and the second curved surface having different bending directions; and
an inflection point located between the first curved surface and the second curved surface, and wherein a distance from the endpoint along the plane portion to an intersection of a straight line vertically extending from the inflection point to the plane portion is longer than a distance from the inflection point to the plane portion.

2. The medical elongated body according to claim 1, wherein the curved surface of the at least one of the two side portions is connected to the plane portion.

3. The medical elongated body according to claim 1, wherein the first curved surface and the second curved surface are in a point symmetric shape.

4. The medical elongated body according to claim 1, further comprising:
an intermediate plane portion, the intermediate plane portion linearly extending between the first curved surface and the second curved surface.

5. The medical elongated body according to claim 4, further comprising:
a spiral on which a plurality of the intermediate plane portions is aligned is disposed at a position different from other spirals on which a plurality of the plane portions is aligned, and the spiral being parallel to the other spirals.

6. The medical elongated body according to claim 1, wherein the angle between the each of the side portions and the plane portion is larger than an angle between a straight line connecting the endpoint and the inflection point and the plane portion.

7. The medical elongated body according to claim 1, further comprising:
each of the endpoints being located at an end of both sides of the first convex portion wherein the two endpoints extend in the circumferential direction.

8. A medical elongated body comprising:
a tube shaped body provided with a belt portion which is a plate member extending in a spiral shape, the belt portion having two side surfaces, each of the two side surfaces having a mountain shape and a valley shape;
each of the mountain shape and the valley shape having a width wider in an extending direction of the belt portion at a top surface side of the mountain shape and at a bottom side of the valley shape;
a plurality of connection surfaces, wherein each of the connection surfaces connecting the top surface side of the mountain shape and a bottom surface of the valley shape, the connection surfaces having an S shape;
wherein the connection surfaces of the top surface side of the mountain shape and the bottom surface of the valley shape have tangential discontinuity in which each of the connection surfaces has an endpoint with the top surface side of the mountain shape and the bottom surface of the valley shape and an angle between the each of the connection surfaces and the top surface side of the mountain shape and the bottom surface of the valley shape is 90 degrees or less; and an inflection point on each of the connection surfaces, and wherein a distance from the endpoint with the top surface side of the mountain shape and the bottom surface of the valley shape along the top surface side of the mountain shape and the bottom side of the valley shape to an intersection of a straight line vertically extending from the inflection point to the top surface side of the mountain shape and the bottom side of the valley shape is longer than a distance from the inflection point to the top surface side of the mountain shape and the bottom side of the valley shape.

9. The medical elongated body according to claim 8, wherein the mountain shape and the valley shape each have a same shape.

10. A method of cutting a calcified lesion area in a blood vessel, the method comprising:

directing a medical elongated body in the blood vessel to a proximal side of the of the calcified lesion area, the medical elongated body including an elongated shaft portion and a cutting portion, the elongated shaft portion having a tube shaped body having a slit extending in a spiral shape, the slit being formed from a first opposing surface and a second opposing surface, the first opposing surface forming a first convex portion, the first convex portion having a wide portion having a width widening in a circumferential direction of the tube shaped body, the second opposing surface forming a concave portion that surrounds and accommodates the wide portion of the first convex portion, the first convex portion having a plane portion and two side portions, the two side portion being connected to both end portions of the plane portion of the first convex portion in the circumferential direction, and wherein the two side portions and the plane portion have tangential discontinuity in which each of the two sides portions have an endpoint with the plane portion and an angle between the each of the side portions and the plane portion is 90 degrees or less, at least one of the two side portions having a curved surface, the curved surface having a first curved surface and a second curved surface, the first curved surface and the second curved surface having different bending directions, and an inflection point located between the first curved surface and the second curved surface, and wherein a distance from the endpoint along the plane portion to an intersection of a straight line vertically extending from the inflection point to the plane portion is longer than a distance from the inflection point to the plane portion;

advancing the elongated shaft portion and the cutting portion into the lesion area;

rotating the elongated shaft portion and the cutting portion; and causing the cutting portion to come into contact with the lesion area and cutting the lesion area.

11. The method according to claim 10, comprising:

causing the cutting portion to rotate in one direction in the lesion area; and causing the cutting portion to rotate in an opposite direction in the lesion area.

12. The method according to claim 10, comprising:

collecting the cut lesion area in a filter; and discharging the cut lesion area in the filter to an outside of the blood vessel.

13. The method according to claim 10, comprising:

aspirating and discharging the cut lesion area to an outside of the blood vessel.

14. The method according to claim 10, comprising:

stopping the rotation of the elongated shaft portion and the cutting portion; and removing the elongated shaft portion and the cutting portion from the blood vessel.

15. The method according to claim 10, wherein at least one of the two side portions has a curved surface, and the curved surface of the at least one of the two side portions is connected to the plane portion.

16. The method according to claim 15, wherein the curved surface has a first curved surface and a second curved surface, the first curved surface and the second curved surface having different bending directions.

* * * * *